United States Patent
Beckham et al.

(10) Patent No.: US 11,136,601 B2
(45) Date of Patent: Oct. 5, 2021

(54) CONVERSION OF S-LIGNIN COMPOUNDS TO USEFUL INTERMEDIATES

(71) Applicant: Alliance for Sustainable Energy, LLC, Golden, CO (US)

(72) Inventors: Gregg Tyler Beckham, Golden, CO (US); Christopher W. Johnson, Denver, CO (US); Sandra Fabienne Notonier, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 53 days.

(21) Appl. No.: 16/530,539

(22) Filed: Aug. 2, 2019

(65) Prior Publication Data

US 2020/0071731 A1    Mar. 5, 2020

Related U.S. Application Data

(60) Provisional application No. 62/713,640, filed on Aug. 2, 2018.

(51) Int. Cl.
| | |
|---|---|
| *C12P 7/22* | (2006.01) |
| *C12N 1/20* | (2006.01) |
| *C12P 7/42* | (2006.01) |
| *C12P 5/00* | (2006.01) |
| *C12N 15/78* | (2006.01) |
| *C12R 1/39* | (2006.01) |
| *C12R 1/40* | (2006.01) |

(52) U.S. Cl.
CPC ............... *C12P 7/22* (2013.01); *C12N 1/20* (2013.01); *C12N 15/78* (2013.01); *C12P 5/002* (2013.01); *C12P 7/42* (2013.01); *C12R 1/39* (2013.01); *C12R 1/40* (2013.01); *C12P 2203/00* (2013.01); *C12Y 114/13082* (2013.01); *C12Y 301/01057* (2013.01)

(58) Field of Classification Search
None
See application file for complete search history.

(56) References Cited

U.S. PATENT DOCUMENTS

| | | | |
|---|---|---|---|
| 1,594,389 | A | 8/1926 | Thellier |
| 1,888,025 | A | 11/1932 | Bent |
| 2,037,001 | A | 4/1936 | Aronovsky |
| 2,042,705 | A | 6/1936 | Dreyfus |
| 3,888,727 | A | 6/1975 | Kenig |
| 3,932,207 | A | 1/1976 | Fogarassy |
| 4,259,444 | A | 3/1981 | Chakrabarty |
| 4,480,034 | A | 10/1984 | Hsieh |
| 4,520,105 | A | 5/1985 | Sinner et al. |
| 4,594,130 | A | 6/1986 | Chang et al. |
| 4,731,328 | A | 3/1988 | Maxwell |
| 4,952,501 | A | 8/1990 | Jasin et al. |
| 5,487,987 | A | 1/1996 | Frost et al. |
| 5,730,837 | A | 3/1998 | Black et al. |
| 6,426,438 | B1 | 7/2002 | Fischer et al. |
| 8,133,704 | B2 | 3/2012 | Baynes et al. |
| 8,211,683 | B2 | 7/2012 | Mase et al. |
| 9,206,445 | B2 | 12/2015 | Yang et al. |
| 9,790,249 | B2 | 10/2017 | Beckham et al. |
| 10,017,792 | B2 | 7/2018 | Beckham et al. |
| 10,253,338 | B2 | 4/2019 | Beckham et al. |
| 10,266,852 | B2 | 4/2019 | Beckham et al. |
| 10,337,034 | B2 | 7/2019 | Beckham et al. |
| 2013/0030215 | A1 | 1/2013 | Bui et al. |
| 2014/0107381 | A1 | 4/2014 | Beckham et al. |
| 2014/0186902 | A1 | 7/2014 | Botes et al. |
| 2014/0193868 | A1 | 7/2014 | Sabirova et al. |
| 2014/0273104 | A1 | 9/2014 | Paripati et al. |
| 2014/0302573 | A1 | 10/2014 | Burk et al. |

FOREIGN PATENT DOCUMENTS

| | | |
|---|---|---|
| WO | 2011/017560 A1 | 2/2011 |
| WO | 2012/106257 A1 | 8/2012 |

OTHER PUBLICATIONS

Masail (A Novel Tetrahydrofolate-Dependent O-Demethylase Gene Is Essential for Growth of Sphingomonas paucimobilis SYK-6 with Syringate. Journal of Bacteriology, May 2004, p. 2757-2765 (Year: 2004).*
Nishikawa et al (Cloning and Sequencing of the Sphingomonas (Pseudomonas) paucimobilis Gene Essential for the O Demethylation of Vanillate and Syringate. Applied and Environmental Microbiology, 0099-2240/98/$04.0010 Mar. 1998, p. 836-842 (Year: 1998).*
Muconolactone isomerase [Pseudomonas putida] GenBank BAA23629.1 Retrieved on Oct. 27, 2017. Published on Nov. 27, 1997 (Year: 1997).
Phenol monooxygenase [Plasmid pEST1226] GenBank AAC64901.1 Retrieved on Oct. 27, 2017. Published Jan. 12, 2007 (Year: 2007).
Muconate cycloisomerase [Pseudomonas putida KT2440] GenBank AAN691312.1 Retrieved on Oct. 27, 2017. Published on Mar. 5, 2010 (Year: 2010).
Protocatechuate 3,4-dioxygenase, beta subunit [Pseudomonas putida F1] GenBank ABQ80638.1 Retrieved on Oct. 27, 2017. Published Jun. 3, 2011 (Year: 2011).

(Continued)

*Primary Examiner* — Kagnew H Gebreyesus

(74) *Attorney, Agent, or Firm* — Sam J. Barkley; Michael A. McIntyre

(57) ABSTRACT

The present disclosure relates to a genetically modified microbial cell that includes a genetic modification resulting in the expression of a vanillate demethylase, where the microbial cell is capable of metabolizing at least one S-lignin decomposition molecule including at least one of syringate and/or 3-O-methyl gallate, and the genetically modified microbial cell is capable of producing gallate. In some embodiments of the present disclosure, the vanillate demethylase may include VanAB.

16 Claims, 23 Drawing Sheets

Specification includes a Sequence Listing.

(56) References Cited

OTHER PUBLICATIONS

Abe et al., "A Tetrahydrofolate-Dependent O-Demethylase, LigM, is Crucial for Catabolism of Vanillate and Syringate in Sphingomonas paucimobilis SYK-6", Journal of Bacteriology, Mar. 2005, vol. 187, No. 6, pp. 2030-2037.
Alén et al., "Gas-liquid Chromatographic Separation of Hydroxy Monocarboxylic Acids and Dicarboxylic Acids on a Fused-silica Capillary Column", Journal of Chromatography A, 1984, vol. 301, pp. 273-276.
Alonso et al., "Bimetallic Catalysts for Upgrading of Biomass to Fuels and Chemicals", Chemical Society Reviews, 2012, vol. 41, pp. 8075-8098.
Anderson et al., "Occurrence, Metabolism, Metabolic Role, and Industrial Uses of Bacterial Polyhydroxyalkanoates" Microbial Reviews, Dec. 1990, vol. 54, No. 2, pp. 450-472.
Bang et al., "DO-Stat Fed-Batch Production of cis, cis-Muconic Acid from Benzoic Acid by Pseudomonas putida BM014", Journal of Fermentation and Bioengineering, 1995, vol. 79, No. 4, pp. 381-383.
Bechthold et al., "Succinic Acid: A New Platform Chemical for Biobased Polymers from Renewable Resources", Chemical Engineering and Technology, May 2008, vol. 31, No. 5, pp. 647-654.
Bonawitz et al., "Disruption of Mediator Rescues the Stunted Growth of a Lignin-deficient *Arabidopsis* Mutant", Nature, May 2014, vol. 509, pp. 376-380.
Bozell et al., "Solvent fractionation of renewable woody feedstocks: Organosolv generation of biorefinery process streams for the production of biobased chemicals", Biomass and Bioenergy, 2011, vol. 35, pp. 4197-4208.
Chen et al., "Lignin Modification Improves Fermentable Sugar Yields for Biofuel Production", Nature Biotechnology, Jul. 2007, vol. 25, No. 7, pp. 759-761.
Chundawat et al., "Deconstruction of Lignocellulosic Biomass to Fuels and Chemicals", Annual Reviews Chemical and Biomolecular Engineering, 2011, vol. 2, pp. 121-145.
Ciesielski et al., "Engineering Plant Cell Walls: Tuning Lignin Monomer Composition for Deconstructable Biofuel Feedstocks or Resilient Biomaterials", Green Chemistry, 2014, vol. 16, pp. 2627-2635.
Dabrowski et al., "Adsorption of Phenolic Compounds by Activated Carbon—A Critical Review", Chemosphere, 2005, vol. 58, pp. 1049-1070.
Daniel et al., "Biochemistry of Coenzyme B12-dependent Glycerol and Diol Dehydratases and Organization of the Encoding Genes", FEMS Microbiology Reviews, 1999, vol. 22, pp. 553-566.
Davis et al., "Process Design and Economics for the Conversion of Lignocellulosic Biomass to Hydrocarbons: Dilute-acid and Enzymatic Deconstruction of Biomass to Sugars and Biological Conversion of Sugars to Hydrocarbons", NREL Technical Report NREL/TP-5100-60223, Oct. 2013, pp. 1-147.
De Boer et al., "The tac promoter: A functional hybrid derived from the trp and lac promoters", Proceedings of the National Academy of Sciences of the United States of America, Jan. 1983, vol. 80, pp. 21-25.
Draths et al., "Environmentally Compatible Synthesis of Adipic Acid from D-glucose", Journal of the American Chemical Society, 1994, vol. 116, No. 1, pp. 399-400.
Dunworth et al., "Investigations on the Mechanism of Catalytic Hydrogenations—XVII. Reductions with Rhodium on Activated Carbon", Journal of the American Chemical Society, 1952, pp. 1459-1462.
Fort et al., Green Chemistry, "Can Ionic Liquids Dissolve Wood? Processing and Analysis of Lignocellulosic Materials with 1-n-butyl-3-methylimidazolium chloride", 2007, vol. 9, pp. 63-69.
Franz et al., "Effect of Chemical Surface Heterogeneity on the Adsorption Mechanism of Dissolved Aromatics on Activated Carbon", Carbon, 2000, vol. 38, pp. 1807-1819.
Fuchs et al. "Microbial degradation of aromatic compounds—from one strategy to four", Nature Reviews—Microbiology, Nov. 2011, vol. 9, pp. 803-816.
Torres Galvis et al., "Supported Iron Nanoparticles as Catalysts for Sustainable Production of Lower Olefins", Science, Feb. 2012, vol. 335, No. 6070, pp. 835-838.
Gomi et al., "Purification and Characterization of Pyrocatechase from the Catechol-assimilating Yeast *Candida maltosa*", Agricultural and Biological Chemistry, 1988, vol. 52, No. 2, pp. 585-587.
Gurrath et al., "Palladium Catalysts on Activated Carbon Supports Influence of Reduction Temperature, Origin of the Support and Pretreatments of the Carbon Surface", Carbon, 2000, vol. 38, pp. 1241-1255.
Harwood et al., "The β-Ketoadipate Pathway and the Biology of Self-Identity", Annual Review of Microbiology, 1996, vol. 50, pp. 553-590.
Hernández-Arranz et al., "The Translational Repressor Crc Controls the Pseudomonas putida Benzoate and Alkane Catabolic Pathways Using a Multi-tier Regulation Strategy", Environmental Microbiology, Jan. 2013, vol. 15, No. 1, pp. 227-241.
Himmel et al., "Biomass Recalcitrance: Engineering Plants and Enzymes for Biofuels", Science, Feb. 2007, vol. 315, No. 5813, pp. 804-807.
Ji et al., "Direct Catalytic Conversion of Cellulose into Ethylene Glycol Using Nickel-Promoted Tungsten Carbide catalysts", Angewandte Chemie, Oct. 2008, vol. 120, No. 44, pp. 8638-8641.
Jiménez et al., "Genomic Analysis of the Aromatic Catabolic Pathways from Pseudomonas putida KT2440", Environmental Microbiology, Dec. 2002, vol. 4, No. 12, pp. 824-841.
Karp et al., "Alkaline Pretreatment of Corn Stover: Bench-Scale Fractionation and Stream Characterization", ACS Sustainable Chemistry Engineering, 2014, vol. 2, No. 6, pp. 1481-1491.
Keenan et al., "Polyhydroxyalkanoate Copolymers from Forest Biomass", The Journal of Industrial Microbiology and Biotechnology, 2006, vol. 33, pp. 616-626.
Kelada et al., "δ-Aminolevulinic Acid Dehydratase Genotype and Lead Toxicity: A HuGE Review", American Journal of Epidemiology, Jul. 1, 2001, vol. 154, No. 1, pp. 1-13.
Kim et al., PHAs Produced by Pseudomonas putida and Pseudomonas oleovorans Grown with n-Alkanoic Acids Containing Aromatic Groups, Macromolecules, 1999, vol. 32, pp. 6058-6064.
Korhonen et al., "Hydrophobic Nanocellulose Aerogels as Floating, Sustainable, Reusable, and Recyclable Oil Absorbent", ACS Applied Materials & Interfaces, May 2011, vol. 3, No. 6, pp. 1813-1816.
Lee et al., "Preparation of alkyl (R)-(−)-3-hydroxybutyrate by acidic alcoholysis of poly-(R)-(−)-3-hydroxybutyrate", Enzyme and Microbial Technology, 2000, vol. 27, pp. 33-36.
Li et al., "One Step Recovery of Succinic Acid from Fermentation Broths by Crystallization", Separation and Purification Technology, 2010, vol. 72, pp. 294-300.
Linger et al., "Lignin Valorization through Integrated Biological Funneling and Chemical Catalysis", Proceedings of the National Academy of Sciences of the United States of America, Aug. 2014, vol. 111, No. 33, pp. 12013-12018.
Luque et al., "Chemical Transformations of Succinic Acid Recovered from Fermentation Broths by a Novel Direct Vacuum Distillation-Crystallisation Method", Green Chemistry, 2009, vol. 11, pp. 193-200.
Madon et al., "Experimental Criterion for the Absence of Artifacts in the Measurement of Rates of Heterogeneous Catalytic Reactions", Industrial & Engineering Chemistry Fundamentals, 1982, vol. 21, No. 4, pp. 438-447.
Martínez et al., "Biodegradation of Lignocellulosics: Microbial, Chemical, and Enzymatic Aspects of the Fungal Attack of Lignin", International Microbiology, Sep. 2005, vol. 8, No. 3, pp. 195-204.
Marx, "Development of a Broad-host-range SacB-based Vector for Unmarked Allelic Exchange", BioMed Central Research Notes, 2008, vol. 1, pp. 1-8.
Morales et al., "The Pseudomonas putida Crc Global Regulator Controls the Expression of Genes from Several Chromosomal Catabolic Pathways for Aromatic Compounds", Journal of Bacteriology, Mar. 2004, vol. 186, No. 5, pp. 1337-1344.

(56) References Cited

OTHER PUBLICATIONS

Moreno et al., "The Pseudomonas putida Crc Global Regulator Controls the Hierarchical Assimilation of Amino Acids in a Complete Medium: Evidence from Proteomic and Genomic Analyses", Proteomics, Jun. 2009, vol. 9, Vo. 11, pp. 2910-2928.

Mu et al., "Lignin Pyrolysis Components and Upgrading—Technology Review", BioEnergy Research, Dec. 2013, vol. 6, No. 4, pp. 1183-1204.

Myung et al., "Disassembly and Reassembly of Polyhydroxyalkanoates: Recycling Through Abiotic Depolymerization and Biotic Repolymerization", Bioresource Technology, 2014, vol. 170, pp. 167-174.

Nelson et al., "Complete Genome Sequence and Comparative Analysis of the Metabolically Versatile Pseudomonas putida KT2440", Environmental Microbiology, Dec. 2002, vol. 4, No. 12, pp. 799-808.

Niu et al., "Benzene-Free Synthesis of Adipic Acid", Biotechnology Progress, 2002, vol. 18, No. 2, pp. 201-211.

Nordlund et al., "Complete Nucleotide Sequence and Polypeptide Analysis of Multicomponent Phenol Hydroxylase from *Pseudomonas* sp. Strain CF600", Journal of Bacteriology, Dec. 1990, vol. 172, No. 12, pp. 6826-6833.

Ornston et al., "Properties of an Inducible Uptake System for ß-Ketoadipate in Pseudomonas putida", Journal of Bacteriology, Feb. 1976, vol. 125, No. 2, pp. 475-488.

Parsell et al., "Cleavage and Hydrodeoxygenation (HDO) of C—O Bonds Relevant to Lignin Conversion Using Pd/Zn in Synergistic Catalysis", Chemical Science, 2013, vol. 4, pp. 806-813.

Peters et al., Acquisition of a Deliberately Introduced Phenol Degradation Operon, pheBA, by Different Indigenous *Pseudomonas* Species, Applied and Environmental Microbiology, Dec. 1997, vol. 63, No. 12, pp. 4899-4906.

Polen et al., "Toward Biotechnological Production of Adipic Acid and Precursors from Biorenewables", Journal of Biotechnology, 2013, vol. 167, No. 2, pp. 75-84.

Prasomsri et al., "Effective Hydrodeoxygenation of Biomass-Derived Oxygenates into Unsaturated Hydrocarbons by MoO3 Using Low H2 Pressure", Energy & Environmental Science, 2013, vol. 6, pp. 1732-1738.

Ragauskas et al., "Lignin Valorization: Improving Lignin Processing in the Biorefinery", Science, 2014, vol. 344, No. 6185, 1246843.

Salis et al., "Automated Design of Synthetic Ribosome Binding Sites to Control Protein Expression", Nature Biotechnology, Oct. 2009, vol. 27, No. 10, pp. 946-950.

Schäfer et al., "Small Mobilizable Multi-purpose Cloning Vectors Derived from the *Escherichia coli* Plasmids pK18 and pK19: Selection of Defined Deletions in the Chromosome of Corynebacterium glutamicum", Gene, Jul. 22, 1994, vol. 145, No. 1, pp. 69-73.

Schweigert et al., "Chemical Properties of Catechols and their Molecular Modes of Toxic Action in Cells, from Microorganisms to Mammals", Environmental Microbiology, 2001, vol. 3, No. 2, pp. 81-91.

Siontes Herrera et al., "Sugar Hydrogenation over a Ru/C Catalyst", Journal of Chemical Technology and Biotechnology, 2011, vol. 86, No. 5, pp. 658-668.

Simmons et al., "Advances in Modifying Lignin for Enhanced Biofuel Production", Current Opinion in Plant Biology, Jun. 2010, vol. 13, No. 3, pp. 312-319.

Sluiter et al., "Compositional Analysis of Lignocellulosic Feedstocks. 1. Review and Description of Methods", Journal of Agriculture and Food Chemistry, 2010, vol. 58, pp. 9043-9053.

Somorjai et al., "Advancing the Frontiers in Nanocatalysis, Biointerfaces, and Renewable Energy Conversion by Innovations of Surface Techniques", Journal of the American Chemical Society, 2009, vol. 131, No. 46, pp. 16589-16605.

Sonoki et al., "Glucose-Free cis,cis-Muconic Acid Production via New Metabolic Designs Corresponding to the Heterogeneity of Lignin", ACS Sustainable Chemistry & Engineering, 2018, vol. 6, No. 1, pp. 1256-1264.

Sparnins et al., "Alternative Routes of Aromatic Catabolism in Pseudomonas acidovorans and Pseudomonas putida : Gallic Acid as a Substrate and Inhibitor of Dioxygenases", Journal of Bacteriology, Dec. 1975, vol. 124, No. 3, pp. 1374-1381.

Sturgeon et al., "A Mechanistic Investigation of Acid-Catalyzed Cleavage of Aryl-Ether Linkages: Implications for Lignin Depolymerization in Acidic Environments", ACS Sustainable Chemistry & Engineering, 2014, vol. 2, No. 3, pp. 472-485.

Tack et al., "Metabolism of Gallic Acid and Syringic by Pseudomonas putida", The Journal of Biological Chemistry, Oct. 1972, vol. 247, No. 20, pp. 6483-6443.

Toraya et al., "Radical Catalysis of B12 Enzymes: Structure, Mechanism, Inactivation, and Reactivation of Diol and Glycerol Dehydratases", CMLS Cellular and Molecular Life Sciences, 2000, vol. 57, pp. 106-127.

Urbanus et al., "Intensified Crystallization in Complex Media: Heuristics for Crystallization of Platform Chemicals", Chemical Engineering Science, 2012, vol. 77, pp. 18-25.

Van Duuren et al., "Generation of a catR Deficient Mutant of P. putida KT2440 that Produces cis, cis-Muconate from Benzoate at High Rate and Yield", Journal of Biotechnology, 2011, vol. 156, pp. 163-172.

Van de Vyver et al., "Emerging Catalytic Processes for the Production of Adipic Acid", Catalysis Science & Technology, 2013, vol. 3, pp. 1465-1479.

Vardon et al., "Hydrothermal Catalytic Processing of Saturated and Unsaturated Fatty Acids to Hyrdrocarbons with Glycerol for in situ Hydrogen Production", Green Chem, 2014, vol. 16, No. 3, pp. 1507-1520.

Weber et al., "Biosynthesis of cis, cis-Muconic Acid and Its Aromatic Precursors, Catechol and Protocatechuic Acid, from Renewable Feedstocks by *Saccharomyces cerevisiae*", Applied and Environmental Microbiology, Dec. 2012, vol. 78, No. 23, pp. 8421-8430.

Wu et al., "Microbial Synthesis of cis,cis-muconic Acid from Benzoate by *Sphingobaterium* sp. GCG Generated from Effluent of a Styme Monomer (SM) Production Plant", Enzyme Microbial Technology, Dec. 2004, vol. 35, Nos. 6-7, pp. 598-604.

Wu et al., "Microbial Synthesis of cis,cis-muconic Acid from Benzoate by *Sphingobaterium* sp. Mutants", Biochemical Engineering Journal, 2006, vol. 29, Nos. 1-2, pp. 35-40.

Yoshida et al., "Regioselective carboxylation of catechol by 3,4-dihydroxybenzoate decarboxylase of Enterobacter cloacae P", Biotechnology Letters, 2010, vol. 32, No. 5, pp. 701-705.

Yu et al., "Review of Pt-Based Bimetallic Catalysis: From Model Surfaces to Supported Catalysts", Chemical Reviews, 2012, vol. 112, No. 11, pp. 5780-5817.

Zakzeski et al., "The Catalytic Valorization of Lignin for the Production of Renewable Chemicals", Chemical Reviews, 2010, vol. 110, pp. 3552-3599.

* cited by examiner

CONVERSION OF S-LIGNIN COMPOUNDS TO USEFUL INTERMEDIATES

CROSS-REFERENCE TO RELATED APPLICATIONS

This application claims priority under 35 U.S.C. § 119 to U.S. Provisional Patent Application No. 62/713,640 filed on 2 Aug. 2018, the contents of which are hereby incorporated by reference in their entirety.

CONTRACTUAL ORIGIN

The United States Government has rights in this disclosure under Contract No. DE-AC36-08GO28308 between the United States Department of Energy and Alliance for Sustainable Energy, LLC, the Manager and Operator of the National Renewable Energy Laboratory.

SEQUENCE LISTING

The instant application contains a Sequence Listing which has been submitted via EFS-web and is hereby incorporated by reference in its entirety. The ASCII copy as filed herewith was originally created on 20 Nov. 2019. The ASCII copy as filed herewith is named NREL 18-80_ST25.txt, is 6 kilobytes in size and is submitted with the instant application.

SUMMARY

An aspect of the present disclosure is a genetically modified microbial cell that includes a genetic modification resulting in the expression of a vanillate demethylase, where the microbial cell is capable of metabolizing at least one S-lignin decomposition molecule including at least one of syringate and/or 3-O-methyl gallate, and the genetically modified microbial cell is capable of producing gallate. In some embodiments of the present disclosure, the vanillate demethylase may include VanAB. In some embodiments of the present disclosure, the genetically modified microbial cell may be capable of producing at least one of 2-hydroxy-2H-pyran-4,6-dicarboxylic acid (PDC), (1E,3E)-4-hydroxybuta-1,3-diene-1,2,4-tricarboxylic acid, (1E)-4-oxobut-1-ene-1,2,4-tricarboxylic acid, 2-hydroxy-4-oxobutane-1,2,4-tricarboxylic acid, oxaloacetate, and/or pyruvate.

In some embodiments of the present disclosure, the genetically modified microbial cell may further include a genetic modification resulting in the expression of a 3,4-dioxygenase. In some embodiments of the present disclosure, the 3,4-dioxygenase may include PcaHG. In some embodiments of the present disclosure, the genetically modified microbial cell may further include an endogenous genetic deletion that ablates the expression of a dioxygenase. In some embodiments of the present disclosure, the dioxygenase may include GalA, and the genetically modified microbial cell may be capable of producing PDC.

In some embodiments of the present disclosure, the genetically modified microbial cell may include a bacterium. In some embodiments of the present disclosure, the genetically modified microbial cell comprises at least one of a fungus, a bacterium, and/or a yeast. In some embodiments of the present disclosure, the bacterium may be from the genus Psuedomonas. In some embodiments of the present disclosure, the bacterium may include at least one of *P. putida, P. fluorescens,* and/or *P. stutzeri*. In some embodiments of the present disclosure, the bacterium may originate from *P. putida* KT2440.

In an aspect, disclosed is a method for making at least one of 2-hydroxy-2H-pyran-4,6-dicarboxylic acid (PDC), (1E,3E)-4-hydroxybuta-1,3-diene-1,2,4-tricarboxylic acid, (1E)-4-oxobut-1-ene-1,2,4-tricarboxylic acid, 2-hydroxy-4-oxobutane-1,2,4-tricarboxylic acid, oxaloacetate, or pyruvate comprising exposing a genetically modified microbial cell to a solution containing at least one of S-lignin decomposition molecules, syringate or 3-O-methyl gallate wherein the genetically modified microbial cell comprises a genetic modification that results in the expression of vanillate demethylase. In an embodiment, the vanillate demethylase is VanAB. In another embodiment, the genetically modified microbial cell further includes a genetic modification resulting in the expression of a 3,4-dioxygenase. In an embodiment, 3,4-dioxygenase is PcaHG. In an embodiment, the genetically modified microbial cell further comprises an endogenous genetic deletion that causes a lack of expression of a dioxygenase. In an embodiment, the dioxygenase is GalA, and the genetically modified microbial cell is capable of producing PDC. In another embodiment, the modified microbial cell is capable of production of PDC at a concentration of up to 3.38 mM. In an embodiment, the modified microbial cell is capable of producing up to 3.38 mM PDC after about 72 hours of growth at a yield of up to 68%.

BACKGROUND

Lignin is the most abundant phenolic polymer on Earth found in plant tissue and formed through the polymerization of p-coumaryl, coniferyl and sinapyl alcohols compounds (H-, G-, and S-lignin types, respectively) by combinatorial oxidative radical coupling. *Pseudomonas putida* KT2440, a robust soil bacterium, can utilize aromatics from lignin biomass as carbon and energy sources and has been extensively engineered to convert various lignin-derived aromatics into added-value fuels and chemicals. The S-lignin degradation pathway has been well described and characterized in the Gram-negative bacterium, *Sphingobium* sp. SYK-6, but only a few studies report the capacity of Pseudomonads to grow on syringyl lignin-derived compounds as well. Thus, there remains a need for the development of other microbial strains that are capable of converting H-, G-, and S-lignin derived compounds into useful intermediates capable of being converted to fuels and/or chemicals.

BRIEF DESCRIPTION OF THE DRAWINGS

Some embodiments are illustrated in referenced figures of the drawings. It is intended that the embodiments and figures disclosed herein are to be considered illustrative rather than limiting.

DETAILED DESCRIPTION

The present disclosure may address one or more of the problems and deficiencies of the prior art discussed above.

However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

The present disclosure relates to genetically modified microorganisms including Pseudomonads (including *Pseudomonas putida*), *Acinetobacter* sp., various Rhodococci (e.g., *Rhodococcus erythryopolis*), *Sphingobium* sp., *Saccharomyces cerevisiae, Zygosaccharomyces bailii, Pichia kudriavzevii*, and *Candida glabrata* that have been metabolically engineered to direct various S-lignin-derived molecules to useful intermediates capable of being converted into useful products; e.g. chemicals, fuels, and/or polymers. Examples of S-lignin-derived molecules include syringaldehyde, syringic acid (syringate when deprotonated), 3-O-methyl gallate (3-MGA), and gallic acid (gallate when deprotonated). Another example of an S-lignin derived molecule is 1,3-butadiene-1,2,4-tricarboxylic acid, 4-hydroxy-, 1-methyl ester. Examples of useful intermediates include 2-hydroxy-2H-pyran-4,6-dicarboxylic acid (PDC), 2-oxo-2H-pyran-4,6-dicarboxylic acid, (1E,3E)-4-hydroxybuta-1,3-diene-1,2,4-tricarboxylic acid, (1E)-4-oxobut-1-ene-1,2,4-tricarboxylic acid, and 2-hydroxy-4-oxobutane-1,2,4-tricarboxylic acid.

In particular, as described herein, the S-lignin degradation pathway in *P. putida* KT2440 was characterized by engineering this microorganism for efficient degradation of S-lignin-derived aromatics, as shown by enzymatic characterization, RNA-seq, and proteomics analysis. Among other things, further metabolic engineering steps led to the generation of a strain accumulating PDC, which may be subsequently polymerized. Thus, the work disclosed herein emphasizes the opportunity for the conversion of H/G/S lignin-derived mixtures into compounds of industrial interest (e.g. polymers). In particular, this work illustrates the role of the vanillate demethylase, VanAB, for the conversion of the syringyl-derived monomers syringic acid and 3-MGA, through which S-lignin-derived molecules may be converted to PDC. The role of VanAB was validated by in vitro characterization of this enzyme. We have demonstrated an alternative pathway to generate PDC from gallic acid, using the protocatechuate 3,4-dioxygenase, PcaHG. Furthermore, metabolic engineering was applied to improve the utilization of syringyl lignin-derived molecules by this soil microorganism for growth and pcaHG genes were overexpressed to successfully increase the production of PDC.

Figure 1:
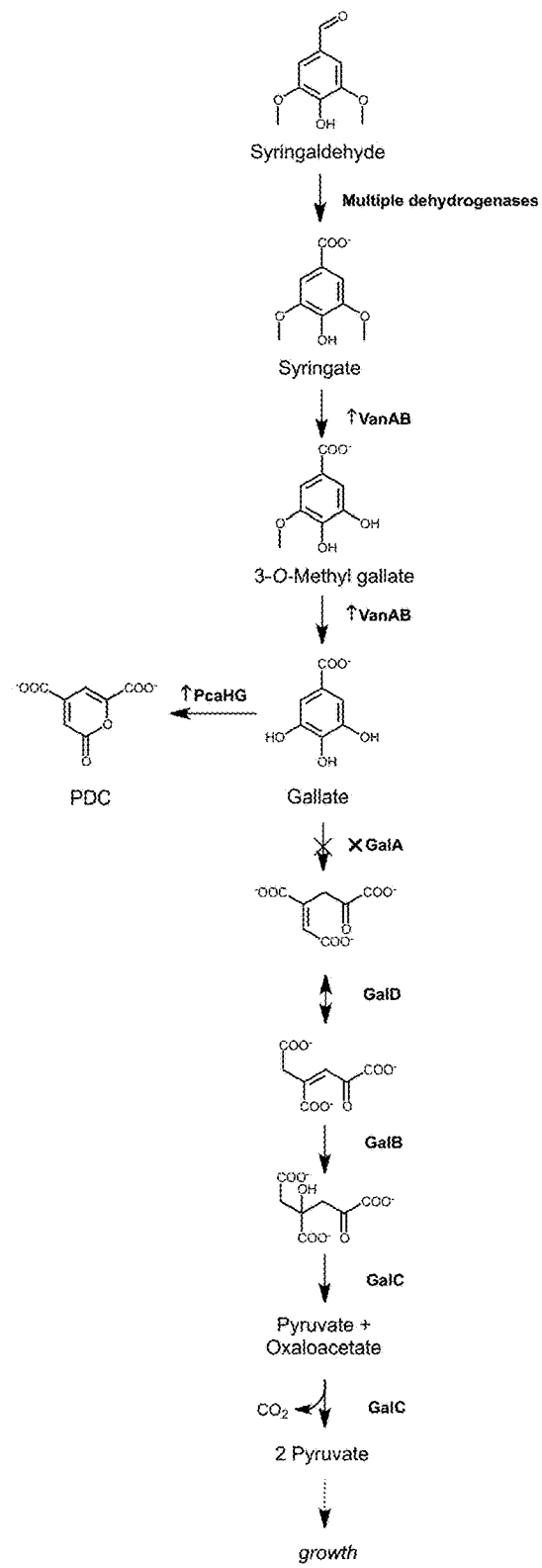
FIG. 1 illustrates a metabolic pathway for converting S-ligin-derived molecules to various intermediates capable of being converted to useful downstream compounds, according to some embodiments of the present disclosure.

FIG. 1 illustrates a genetically engineered microbial pathway, which is shown herein to improve the conversion of S-lignin-derived monomers to PDC and potentially other molecules. In this example, the microbe utilized was *P. putida* KT2440. However, *P. putida* is only one example, and other microbes, including other bacteria, are considered within the scope of the present disclosure. Referring to FIG. 1, S-lignin degradation can result in the formation of syringaldehyde. Syringaldehyde may then be converted to syringate by one or more dehydrogenases. Up-regulation and/or the constitutive expression of a vanillate demethylase, in this case VanAB, can facilitate the conversion of syringate, down the pathway, through 3-MGA to gallate. In one embodiment of the present disclosure, removal of a dioxygenase, in this example GalA, may prevent or minimize the formation of the downstream (1E,3E)-4-hydroxybuta-1,3-diene-1,2,4-tricarboxylic acid, while up-regulation and/or the constitutive expression of a 3,4-dioxygenase, for example PcaHG, may shunt gallate to PDC, thus maximizing PDC production.

Although PDC is described above, this is not a necessary limitation, and it is within the scope of the present disclosure that any S-lignin-derived molecule that can be funneled to at least one of syringaldehyde and/or syringate may be subsequently converted to other useful intermediates using the engineered microbes described herein. For example, for cases where GalA is not removed, inactivated, etc., VanAB expression may enable the production of molecules other than PDC through the syringaldehyde-syringate-3-MGA-gallate pathway, for example, to molecules including at least one of (1E,3E)-4-hydroxybuta-1,3-diene-1,2,4-tricarboxylic acid, (1E)-4-oxobut-1-ene-1,2,4-tricarboxylic acid, 2-hydroxy-4-oxobutane-1,2,4-tricarboxylic acid, oxaloacetate, and/or pyruvate. Thus, a wide variety of S-lignin decomposition products may be converted to a wide variety of useful intermediates, as long as the S-lignin decomposition products are funneled to at least one of syringalhye and/or syringate.

Referring again to FIG. 1, a modified P. *Putida* KT2440 strain for the production of PDC was engineered by deletion of the genes encoding a dioxygenase (e.g. GalA). In addition, the genes encoding an endogenous vanillate demethylase (e.g. VanAB) were upregulated by the addition of a DNA sequence encoding the Ptac promoter fused to and upstream (5') of the DNA sequences encoding the endogenous vanillate demethylase. In addition, the genes encoding an endogenous 3,4-dioxygenase (e.g. PcaHG) were upregulated by the addition of a DNA sequence encoding the Ptac promoter fused to and upstream (5') of the DNA sequences encoding the endogenous 3,4-dioxygenase. As will be shown below, this engineered strain of P. *Putida* KT2440 greatly increased the conversion of S-lignin-derived monomers to PDC. Plasmid construction, bacterial strain construction, and primer details are provided in Tables 1-3.

TABLE 1

Construction details for the plasmids used.

| Plasmid | Utility | Construction details |
| --- | --- | --- |
| pCJ066 | pBTL-2-vanAB overexpressed under the Lac promoter | vanAB (2,102 bp) was amplified from *P. putida* KT2440 genomic DNA with oCJ369 and oCJ370 and assembled into pBTL-2 (2,595 bp) amplified with oCJ160 and oCJ161. |
| pCJ107 | To insert a second copy of vanAB into the genome under the Tac promoter (fpvA locus) | The Ptac:vanAB casette (2125 bp) was amplified from pCJ066 with primers oCJ548/oCJ549 and assembled into pCJ042 digested with AvrII and SpeI (7495 bp). pCJ042 contains the upstream and downstream targeting regions for integration 3' of fpvA, amplified from *P. putida* KT2440 gDNA with primer pairs oCJ301 & oCJ302 and oCJ306 & oCJ307, respectively. The clone was confirmed by diagnostic digest with SalI on Dec. 14, 2015 and by sequencing. |

TABLE 1-continued

Construction details for the plasmids used.

| Plasmid | Utility | Construction details |
|---|---|---|
| pSN66 | Plasmid pK18mobsacB for deletion of vanAB | pk18smobsacB was cut with BamHI and EcoRI for insertion of the targeted regions of upstream and downstream of VanAB and was sent for sequencing and confirmed with primers oCJ290, oCJ291, oSN103, and oSN226. |
| pSN73 | Plasmid pK18mobsacB for deletion of galA | pk18smobsacB was cut with BamHI and EcoRI for insertion of the targeted regions of upstream and downstream of GalA and was sent for sequencing and confirmed with primers oCJ290 and oCJ29. |
| pCJ011 | Plasmid pCM433 for deletion of pcaHG | The 5' targeting region (981 bp) was amplified from *P. putida* KT2440 genomic DNA with primer pair oCJ100/oCJ101 and the 3' targeting region (1040 bp) was amplified using primer pair oCJ102/oCJ103. These fragments were then assembled into pCM433 digested with AatII and SacI (7991 bp). Clone G5. |
| pCJ020 | Plasmid pCM433 for integration of Ptac promoter upstream pcaHG | Plasmid containing upstream region of pcaHG gene, Ptac promoter for integration and pcaHG gene downstream of the promoter Clone B2. |
| pSN82 | pBTL-2-galA overexpressed under the Lac promoter | pBTL-2 plasmid containing GalA under Lac promoter was confirmed by sequencing with primers oCJ054, oCJ163, oCJ534 |
| pSN84 | pBTL-2-pcaHG overexpressed under the Lac promoter | pBTL-2 plasmid containing pcaHG under Lac promoter was confirmed by sequencing with primers oCJ163 and oCJ534 |

TABLE 2

Construction details for bacterial strains used.

| Strain | Genotype | Construction details |
|---|---|---|
| CJ486 | *P. putida* KT2440 fpvA:Ptac:vanAB | Ptac:VanAB was integrated downstream of fpvA by transforming KT2440 with pCJ107. Plasmid integration at the fpvA locus was diagnosed by amplification of a 1496 bp product (3' junction) with primers oCJ312/oCJ550 on Jun. 16, 2016. Following sucrose selection, the gene addition in the isolate was confirmed by amplification of a 1092 bp product at the fpvA locus using primers oCJ311/oCJ312. |
| SN182 | *P. putida* KT2440 Wild-type carrying empty vector pBTL-2 | KT2440 Wild-type was transformed with the plasmid pBTL-2 empty vector. |
| SN183 | *P. putida* KT2440 Wil-type carrying vector pBTL-2 with vanAB gene overexpressed under the Lac promoter | KT2440 Wild-type was transformed with the plasmid pCJ066. |
| SN166 | KT2440 ΔvanAB carrying pBTL-2 vector containing vanAB gene overexpressed under Lac promoter | *P. putida* KT2440 ΔVanAB |
| SN175 | KT2440 ΔvanAB Carrying pBTL-2-vanAB | *P. putida* KT2440 ΔVanAB carrying vector pBTL-2 and gene VanAB overexpressed under the Lac promoter for rescued activity |
| SN249 | *P. putida* KT2440 fpvA:Ptac:vanAB ΔgalA | Deletion of GalA in KT2440 CJ486 based on the addition of pSN73. Correct colony containing the deletion was confirmed by diagnostic PCR with oSN238/239 giving 1556 bp product rather than 2579 bp. |
| SN253 | KT2440 CJ486 Ptac:vanAB in fpvA locus ΔpcaHG | Deletion of pCAHG in strain CJ486, colony 8 was verified by colony PCR with oCJ106/107 (PCR product of 2 kb instead of 3.3 kb in WT) |
| SN255 | *P. putida* KT2440 fpvA:Ptac:vanAB ΔgalA, ΔpcaHG | Deletion of pcaHG in KT2440 SN249 (ΔGalA in CJ486 based strain). Correct colony containing the deletion was confirmed by diagnostic PCR with oCJ106/107 giving 2045 bp product rather than 3381 bp. |

TABLE 2-continued

Construction details for bacterial strains used.

| Strain | Genotype | Construction details |
|---|---|---|
| SN265 | *P. putida* KT2440 fpvA:Ptac:vanAB Ptac:pcaHG | Based on pCJ020, addition of Ptac promoter upstream of pcaHG gene for constitutive expression in CJ486 based strain |
| SN266 | *P. putida* KT2440 fpvA:Ptac:vanAB Ptac:pcaHG ΔgalA | Based on pCJ020, addition of Ptac promoter upstream of pcaHG gene for constitutive expression in SN249 based strain with GalA deleted |
| SNX | *E. coli* carrying the plasmid for VanAB expression | |

TABLE 3

Primers used.

| SEQ ID NO. | Primer | Sequence (5'-3') |
|---|---|---|
| SEQ ID NO: 1 | oCJ369 | gtgagcggataacaatttcacacTCTAGAgAGGAGGACAGCTatgtaccccaaaa acacctggtacgtc |
| SEQ ID NO: 2 | oCJ370 | tggagtctgaggctcgtcctgaatGATATCtcagatgtccagcaccagcagc |
| SEQ ID NO: 3 | oCJ160 | GATATCATTCAGGACGAGCCTCAGACTCC |
| SEQ ID NO: 4 | oCJ161 | CTCTAGAGTGTGAAATTGTTATCCGCTCACAATTCC |
| SEQ ID NO: 5 | oCJ548 | gtgtggaattgtgagcggataacaatttcacac |
| SEQ ID NO: 6 | oCJ549 | GCCTCCGGTCGGAGGCTTTTGACTACTAGTctgaatGATATCtcag atgtccagcaccag |
| SEQ ID NO: 7 | oCJ301 | agtgagcgcaacgcaattaatgtgagttagaagccgaatgtcgatgatatctacaacctgag |
| SEQ ID NO: 8 | oCJ302 | gattaattgtcaacagctcGAATTCaaaaaaccgcacctgggtgcg |
| SEQ ID NO: 9 | oCJ306 | gtaaACTAGTAGTCAAAAGCCTCCGACCGGAGGCTTTTGACTca tggatgcctgaaaggctcccttac |
| SEQ ID NO: 10 | oCJ307 | ccctgagtgcttgcggcagcgtgaagctaggcccctctggagaatcgaacgatg |
| SEQ ID NO: 11 | oCJ290 | AATACGCAAACCGCCTCTC |
| SEQ ID NO: 12 | oCJ291 | GTAGCTGACATTCATCCG |
| SEQ ID NO: 13 | oSN103 | CCACTGCGCCAGCGACGC |
| SEQ ID NO: 14 | oSN226 | GCTTCAGGCGAGTTGGCG |
| SEQ ID NO: 15 | oCJ311 | AGCCTCTTCAGCGTCAAC |
| SEQ ID NO: 16 | oCJ312 | CACGCCTGCTTCATTGAAC |
| SEQ ID NO: 17 | oCJ550 | TGCACCTGTATGTATGCG |
| SEQ ID NO: 18 | oSN238 | tgacctacttcatgggcctg |
| SEQ ID NO: 19 | oSN239 | GAAGTTGAAACGGTCCGAGG |
| SEQ ID NO: 20 | oCJ054 | ATCGGCTCGTATAATGTGTGG |
| SEQ ID NO: 21 | oCJ163 | TTGTCCAGCAGGGTTGTC |
| SEQ ID NO: 22 | oCJ534 | CCTCGGTGAGTTTTCTCC |
| SEQ ID NO: 23 | oCJ100 | ccgaaaagtgccacctGACGTCggccttgctgctgcag |
| SEQ ID NO: 24 | oCJ101 | GCCGCagctcgAGATCTggaattgtgagaacgcctgg |
| SEQ ID NO: 25 | oCJ102 | AGATCTcgagctGCGGCCGCggtgaagcttgggggcc |

TABLE 3-continued

Primers used.

| SEQ ID NO. | Primer | Sequence (5'-3') |
| --- | --- | --- |
| SEQ ID NO: 26 | oCJ103 | gctggatcctctagtGAGCTCacgataccccattgccag |
| SEQ ID NO: 27 | oCJ105 | CACCGAAATCAGCAAGACG |
| SEQ ID NO: 28 | oCJ106 | ATCTTGAACCAACGCACC |

Syringate Utilization by *P. putida* KT2440:

As describe herein, native strains and engineered strains of *P. putida* KT2440 were tested to determine their ability to catalyze the O-demethylation of syringate and subsequently of 3-MGA.

Figure 2:
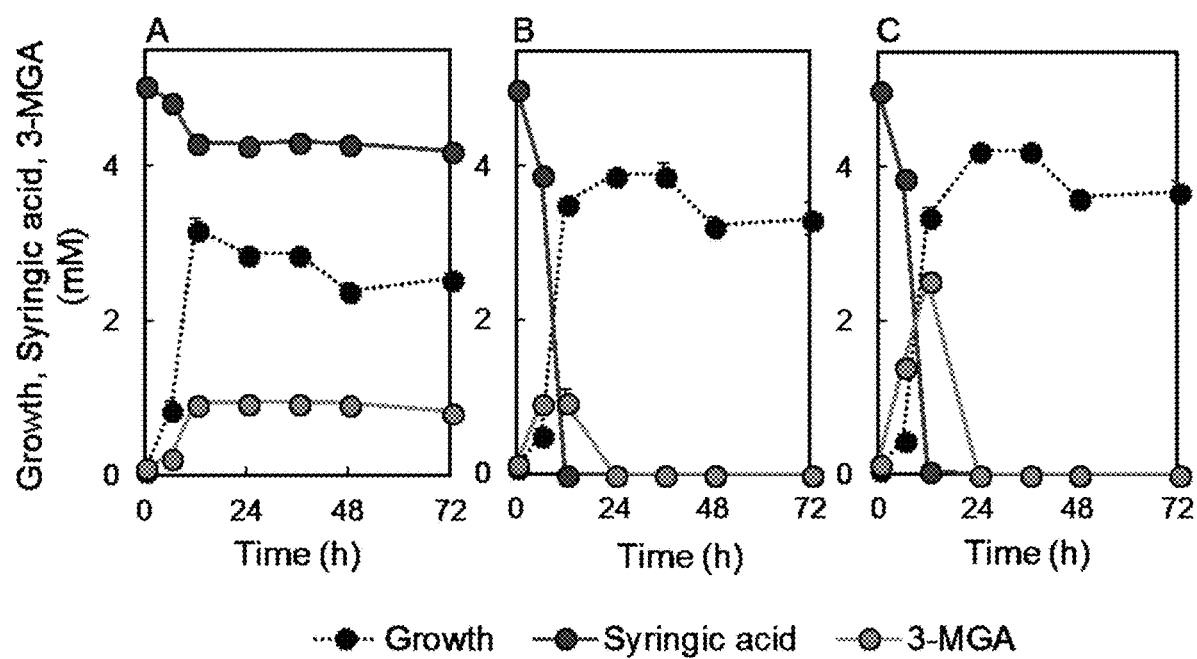
FIG. 2 illustrates growth results for: Panel A. *P. putida* wild-type KT2440; Panel B. CJ486, the engineered strain, CJ486, which expresses a second constitutive copy of the gene encoding the native vanillate 0-demethylase, VanAB; and Panel C. SN183, wild-type *P. putida* KT2440 carrying overexpressed VanAB on plasmid pBTL-2, all according to some embodiments of the present disclosure. Cells were grown in M9 minimal medium containing 5 mM syringate and 20 mM glucose and cultures were sampled periodically to evaluate growth by $OD_{600}$ and metabolite concentrations in the media using HPLC.
Figure 3:
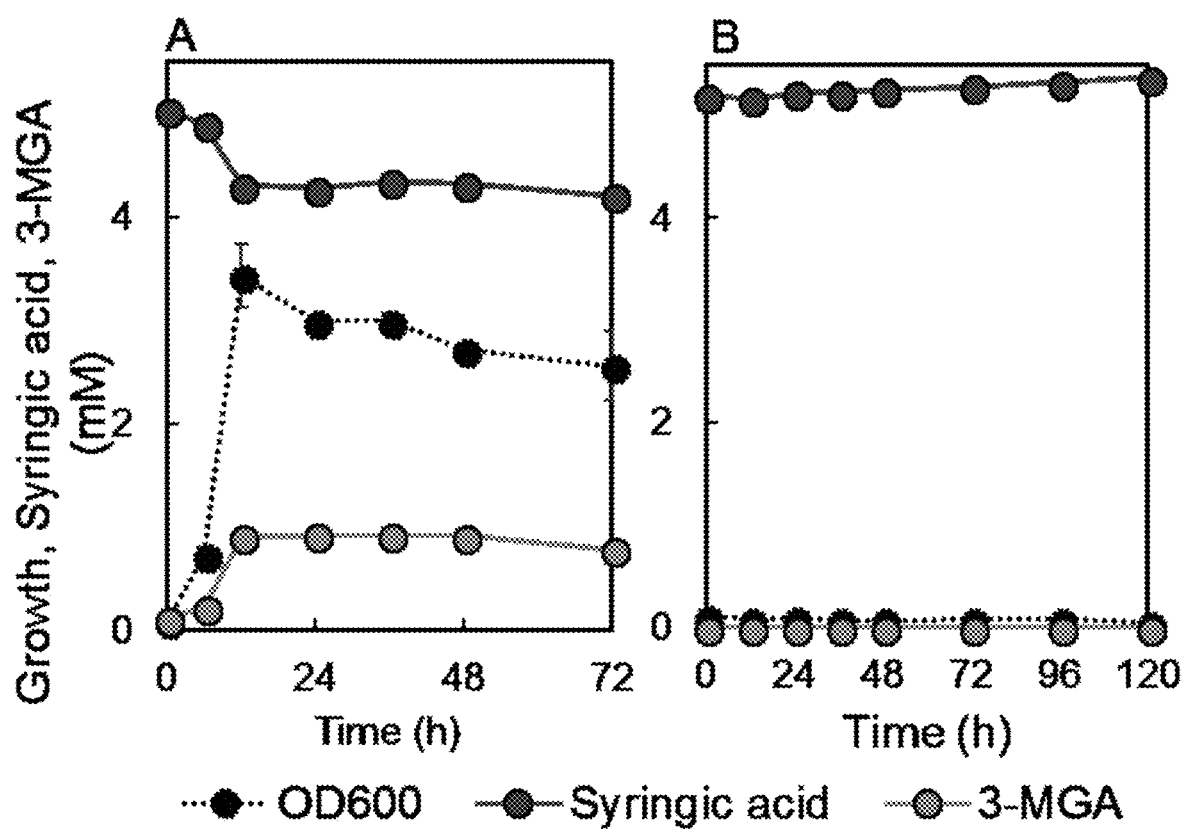
FIG. 3 illustrates growth results for: Panel A. *P. putida* wild-type KT2440 carrying empty vector pBTL-2, grown in M9 minimal medium containing 5 mM syringate and 20 mM glucose; and Panel B. 5 Mm syringate as sole carbon source, both according to some embodiments of the present disclosure. Culture was sampled periodically to evaluate growth by $OD_{600}$ and metabolite concentrations in the media using HPLC.

The results described herein demonstrate that *P. putida* KT2440 wild type (and SN182 KT2440 wild-type carrying empty vector pBTL-2) only partially demethylate syringate natively when syringate was provided as the only source of carbon and energy. The results suggest that VanAB expression may not be sufficient in the presence of syringate and D-glucose to enable substantial metabolism of the substrate (see FIG. 2 Panel A and FIG. 3 Panel A). To test this hypothesis, syringate metabolism was evaluated by an engineered strain of *P. putida* KT2440, CJ486, that contains a second, constitutively expressed copy of the genes encoding VanAB integrated into the genome and SN183, which contains VanAB overexpressed on a plasmid. The two engineered strains overexpressing VanAB show complete conversion of 5 mM of syringate in M9 minimal medium containing 20 mM D-glucose after 12 h of cell cultivation (see FIG. 2 Panels B and C). The two engineered strains also display higher $OD_{600}$ than the WT strain (see FIG. 2 Panel A), providing further evidence that they metabolized the two substrates supplemented. It is worth noting that the intermediate 3-MGA accumulated within the first 12 hours (in higher amounts in SN183) before being further metabolized, suggesting that VanAB is able to demethylate 3-MGA at a lower rate than syringate.

Figure 4:
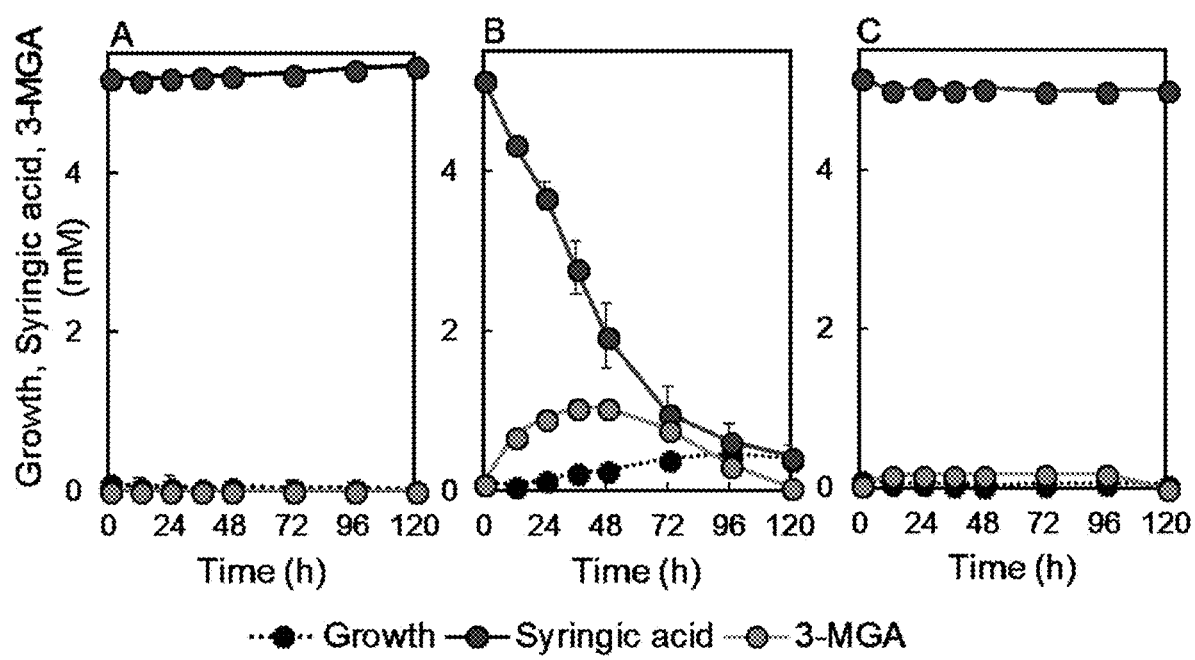
FIG. 4 illustrates: Panel A. *P. putida* wild-type KT2440; Panel B. CJ486, the engineered strain, CJ486, which expresses a second constitutive copy of the gene encoding the native vanillate 0-demethylase, VanAB; and Panel C. SN183, wild-type *P. putida* KT2440 carrying overexpressed VanAB on plasmid pBTL-2, all according to some embodiments of the present disclosure. Cells were grown in M9 minimal medium containing 5 mM syringate as sole carbon source and cultures were sampled periodically to evaluate growth by $OD_{600}$ and metabolite concentrations in the media using HPLC.

The metabolism of syringate by *P. putida* as its sole source of carbon and energy was also evaluated. CJ486 was able to deplete the substrate almost completely after five days (see FIG. 4 Panel B), while the wild-type strains are not able to grow (see FIG. 4 Panel A and FIG. 3 Panel B). Surprisingly SN183, performed as a wild-type strain and no substrate conversion was observed (see FIG. 4 Panel C).

Figure 5:
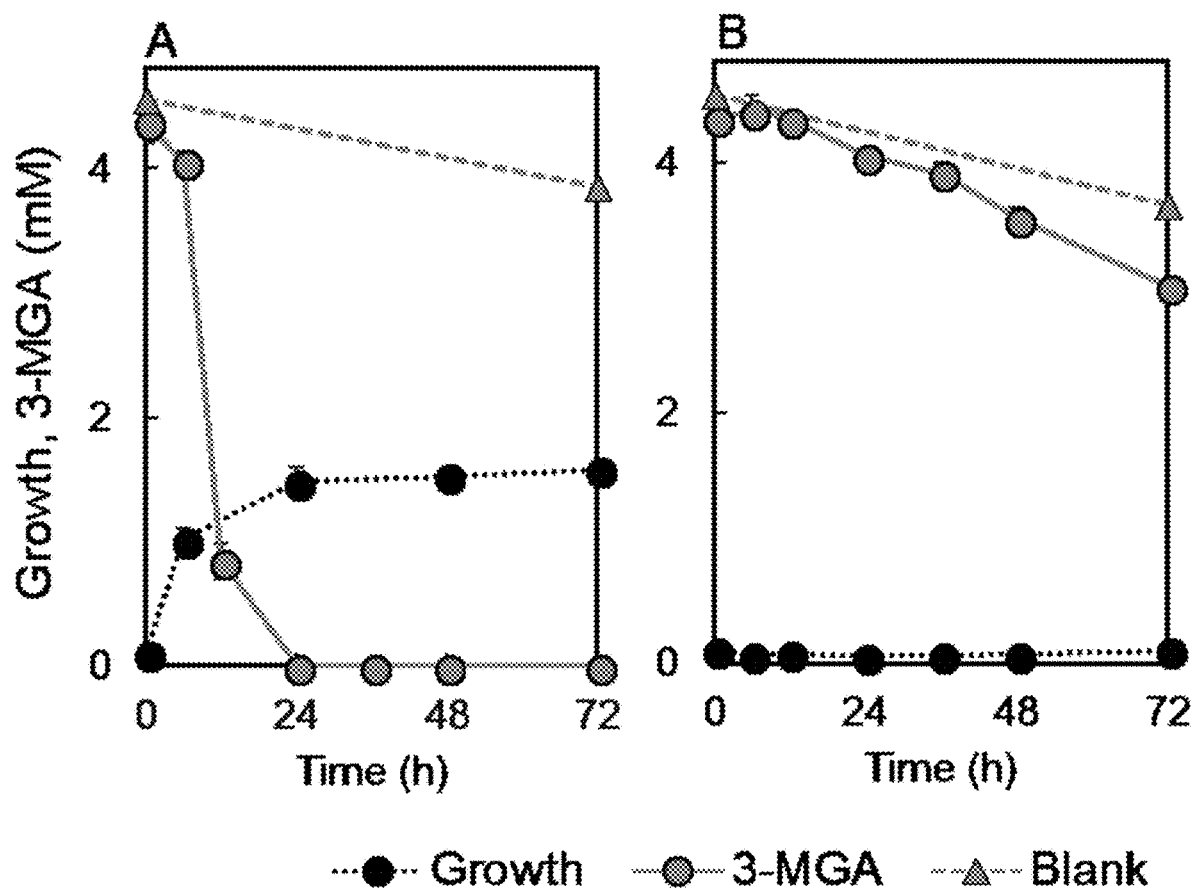
FIG. 5 illustrates: Panel A. Engineered *P. putida* CJ486 (second copy vanAB overexpressed in genome), grown in M9 minimal medium containing 5 mM 3-MGA and 20 mM glucose; and Panel B. 5 Mm 3-MGA as sole carbon source, both according to some embodiments of the present disclosure. Culture was sampled periodically to evaluate growth by $OD_{600}$ and metabolite concentrations in the media using HPLC.
Figure 6:
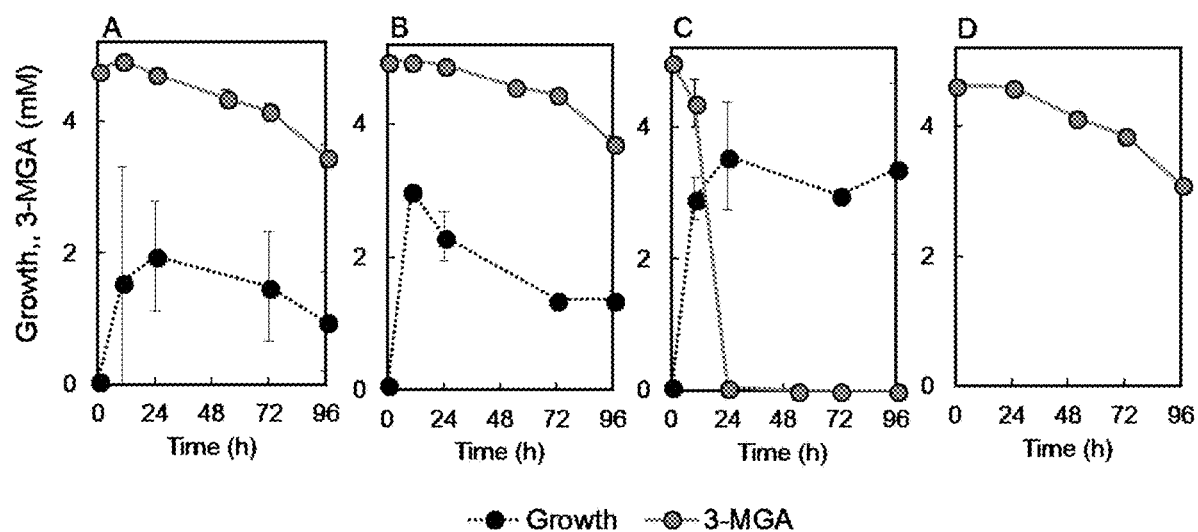
FIG. 6 illustrates: Panel A. *P. putida* wild-type KT2440; Panel B. Engineered strain SN166 (ΔvanAB); Panel C. Engineered strain SN175 (ΔvanAB, carrying overexpressed vanAB on plasmid pBTL-2); and Panel D. Blank, all according to some embodiments of the present disclosure. Cells were grown in M9 minimal medium containing 5 mM 3-MGA and 20 mM glucose. Culture was sampled periodically to evaluate growth by $OD_{600}$ and metabolite concentrations in the media using HPLC and the experiment was down-scaled (in 25 mL flask, 10 mL culture) and performed in duplicate. 3-MGA is unstable molecule that can get oxidized overtime.

3-MGA Utilization by *P. putida* KT2440:

The lower activity rate of VanAB towards 3-MGA intermediate was also demonstrated by feeding the intermediate 3-MGA to the engineered strain in the presence of or absence of glucose (see FIG. 5 Panels A and B, respectively). More than 12 hours were required to enable consumption of the substrate by CJ486 in the presence of glucose and as expected the entire substrate was consumed at a slow rate in the case of 3-MGA as the sole carbon source in comparison to the syringate substrate. Additionally, the experiment of providing 5 mM 3-MGA in the presence of 20 mM glucose was evaluated with the wild-type strain KT2440, the strain SN166 in which VanAB was deleted, and SN175 (SN166-based strain) carrying VanAB enzyme on pBTL-2 plasmid (see FIG. 6 Panels A, B, and C, respectively). The wild-type strain and SN166 activity were unable to efficiently metabolize 3-MGA and the substrate became oxidized overtime (see the blank sample in FIG. 6 Panel D). Only the SN175 strain with VanAB activity rescued on a plasmid and overexpressed was able to consume 3-MGA substrate as the energy and carbon source, within 24 hours (higher $OD_{600}$ displayed).

Figure 7:
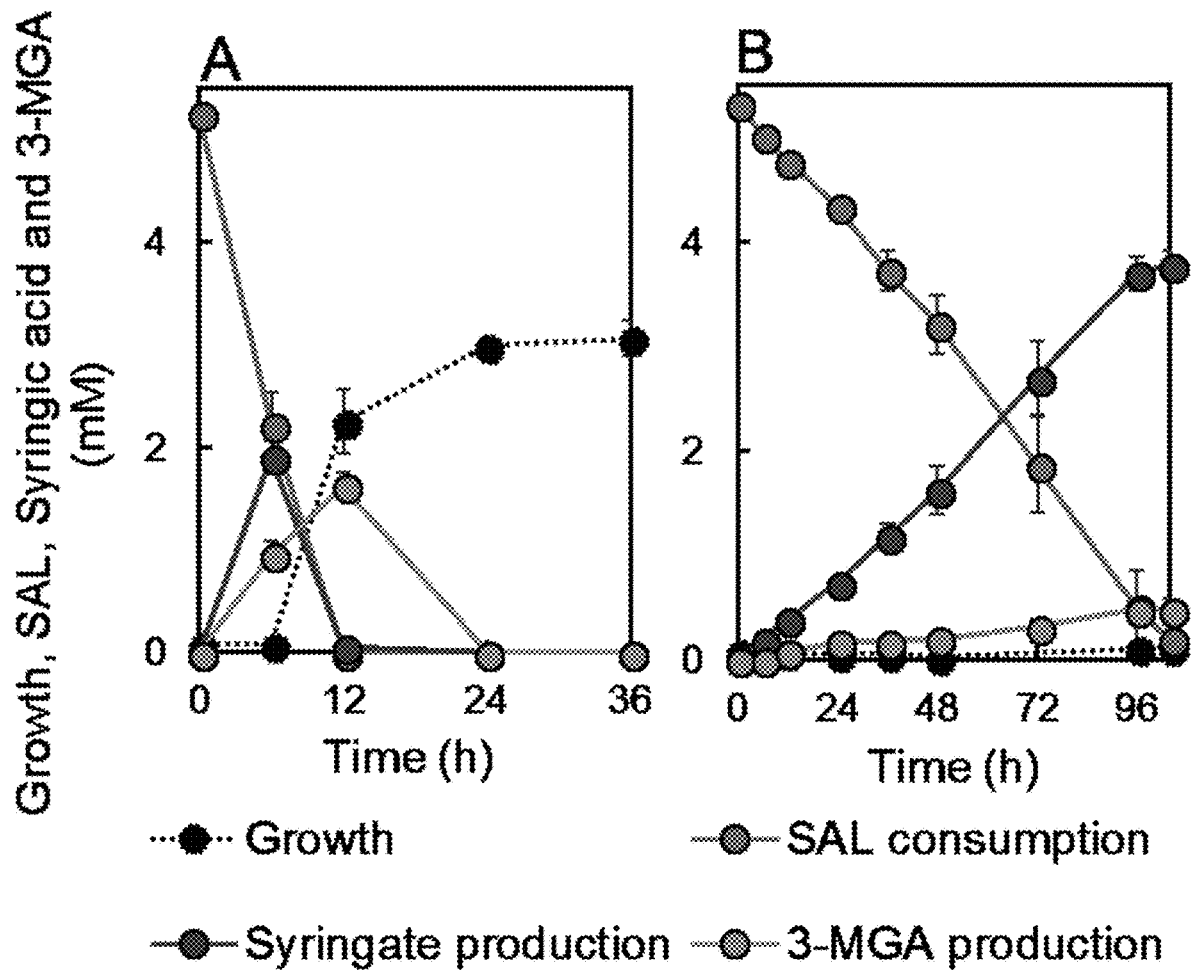
FIG. 7 illustrates results from engineered KT2440, CJ486 grown in M9 minimal medium containing 5 mM SAL in the presence or absence of 20 mM glucose (A and B), according to some embodiments of the present disclosure. Cultures were sampled periodically to evaluate growth by $OD_{600}$ and metabolite concentrations in the media using HPLC.
Figure 8:
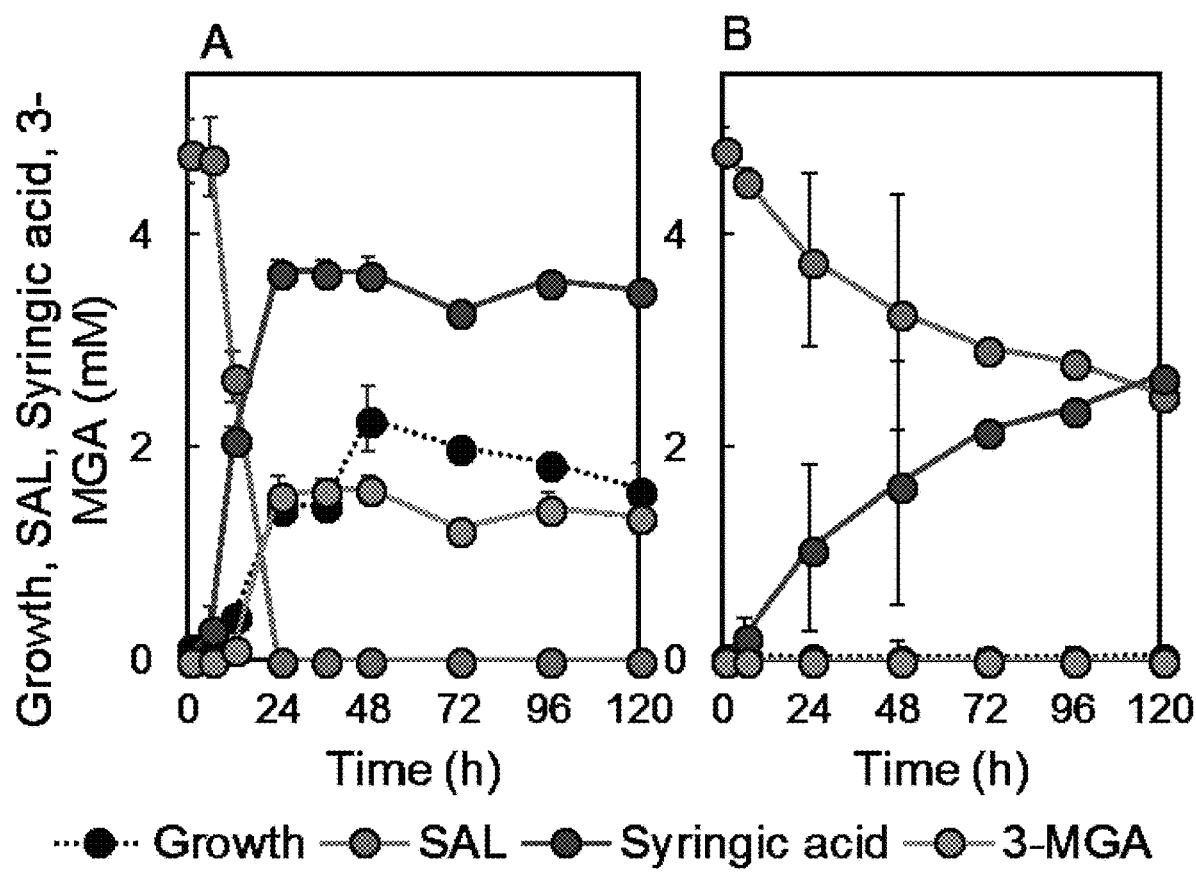
FIG. 8 illustrates: Panel A. *P. putida* wild-type KT2440, grown in M9 minimal medium containing 5 mM SAL and 20 mM glucose; and Panel B. 5 mM SAL as sole carbon source, both according to some embodiments of the present disclosure. Culture was sampled periodically to evaluate growth by $OD_{600}$ and metabolite concentrations in the media using HPLC.

Utilization of Syringaldehyde:

Next, it was examined whether the engineered *P. putida* KT2440 CJ486 was capable of metabolizing the S-derived lignin monomer syringaldehyde (SAL). The engineered strain CJ486 was tested in the presence or absence of 20 mM glucose and 5 mM SAL. The engineered strain was able to entirely metabolize SAL within 12 hours in the presence of glucose, transiently accumulating the intermediates syringic acid and 3-MGA (see FIG. 7 Panel A). In the absence of this other syringaldehyde as the sole carbon and energy source, the complete depletion of SAL occurs after 4 days of cultivation, during which syringic acid and 3-MGA accumulate (see FIG. 7 Panel B). The wild-type was also able to consume SAL in the presence of glucose and this led to the accumulation of syringic acid and 3-MGA, that were not further metabolized (see FIG. 8 Panel A). In the case of wild-type grown on SAL as sole carbon source, there was only a slow conversion into SA and a very small amount of 3-MGA that was not further metabolized, which was unable to support growth (see FIG. 8 Panel B).

Figure 9:
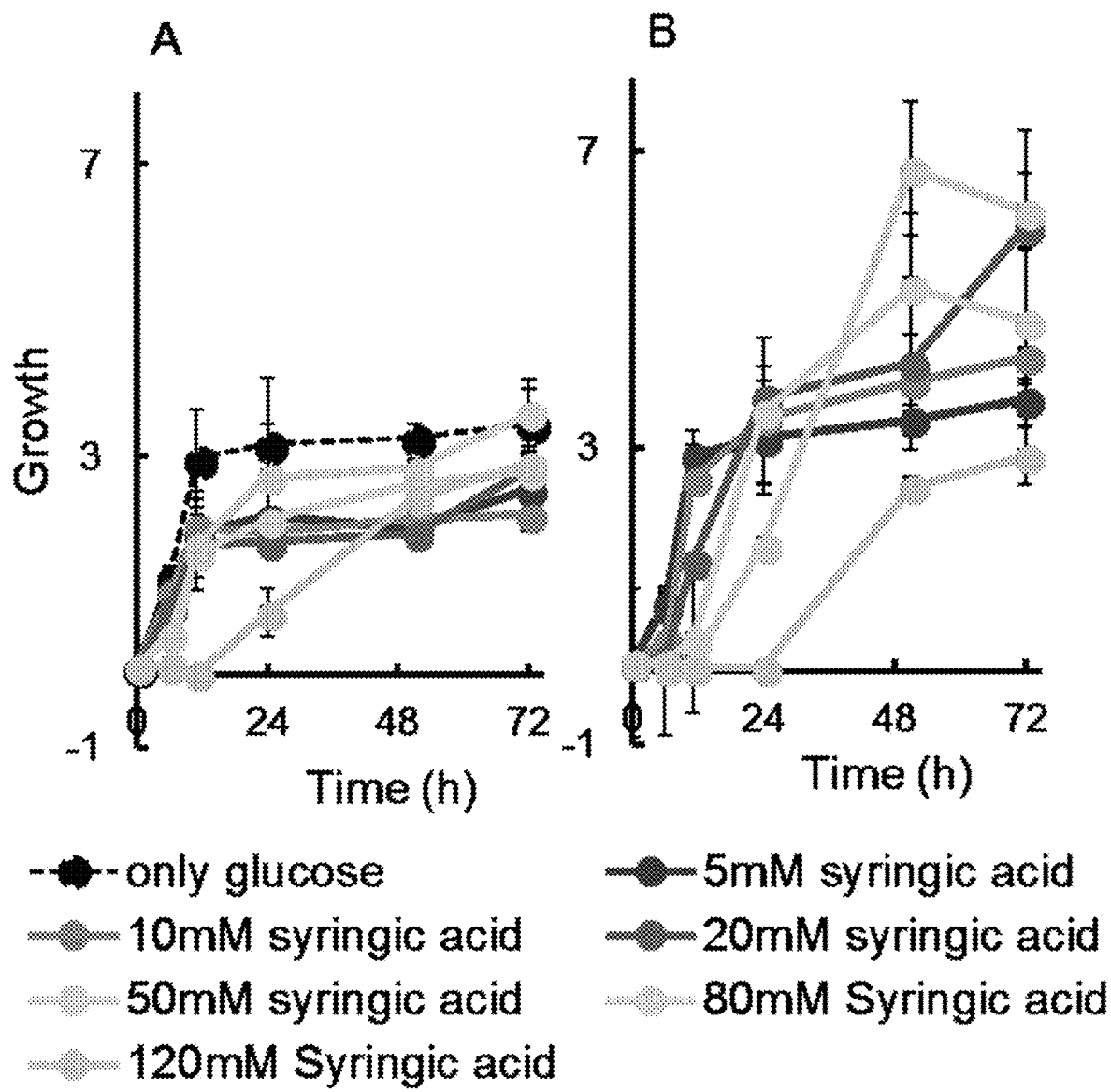
FIG. 9 illustrates: Panel A. Wild-type *P. putida* KT24401 and Panel B. *P. putida* CJ486 (second copy vanAB overexpressed in genome), both according to some embodiments of the present disclosure. Cells were grown in M9 minimal medium containing 20 mM glucose and various concentrations of syringate. Cultures were sampled periodically to evaluate growth by $OD_{600}$ and metabolite concentrations in the media using HPLC. Each point represents the average of two measurements with error bars representing their range.
Figure 10:
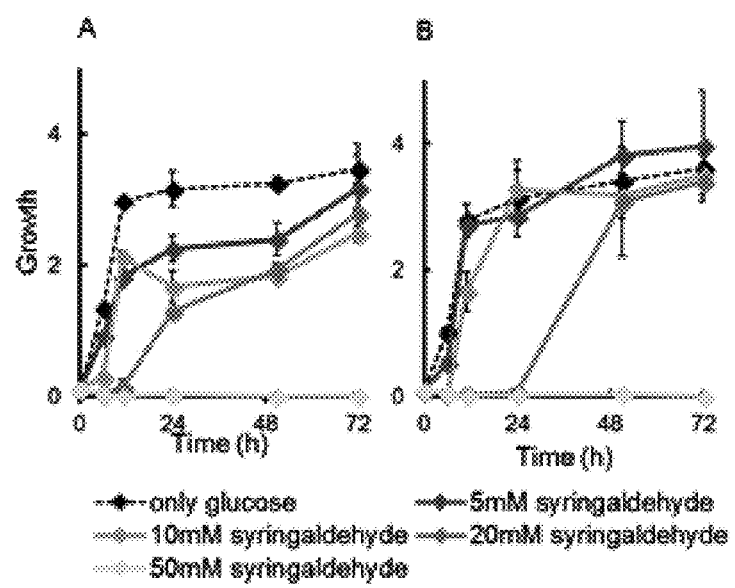
FIG. 10 illustrates: Panel A. Wild-type *P. putida* KT2440; and Panel B. *P. putida* CJ486 (second copy vanAB overexpressed in genome), both according to some embodiments of the present disclosure. Cells were grown in M9 minimal medium containing 20 mM glucose and various concentrations of SAL. Cultures were sampled periodically to evaluate growth by $OD_{600}$ and metabolite concentrations in the media using HPLC. Each point represents the average of two measurements with error bars representing their range.
Figure 11:
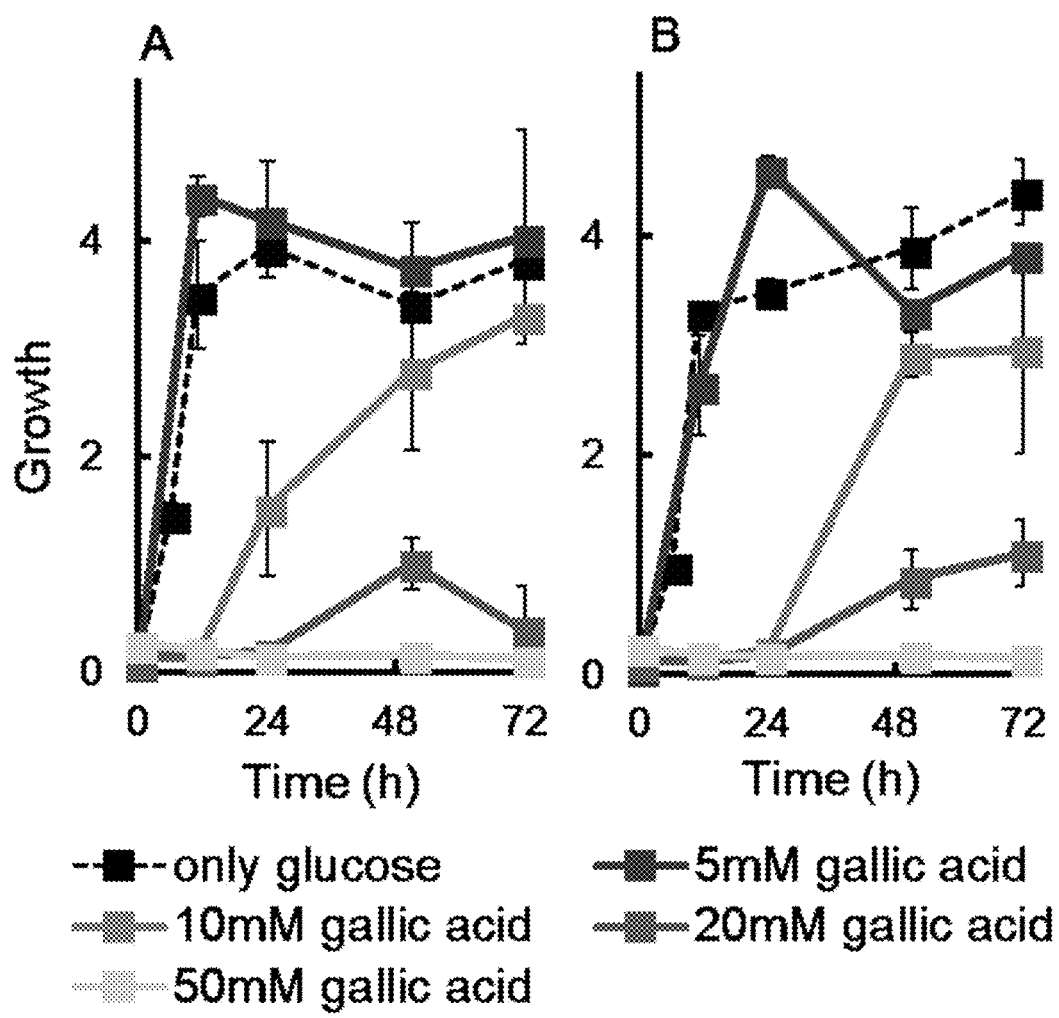
FIG. 11 illustrates: Panel A. Wild-type *P. putida* KT2440; and Panel B. *P. putida* CJ486 (second copy vanAB overexpressed in genome), both according to some embodiments of the present disclosure. Cells were grown in M9 minimal medium containing 20 mM glucose and various concentrations of gallic acid. Cultures were sampled periodically to evaluate growth by $OD_{600}$ and metabolite concentrations in the media using HPLC. Each point represents the average of two measurements with error bars representing their range.

Toxicity Assessment of the S-Lignin Derived Monomers:

Toxicity tolerance of S-lignin monomers syringic acid, SAL and gallate to *P. putida* KT2440 was also assessed. To evaluate this, the engineered strain CJ486 and wild-type strain were grown in M9 minimal media containing 20 mM glucose and various concentrations of the S-lignin monomers. It was found that both CJ486 (see FIG. 9 Panel B) and KT2440 (see FIG. 9 Panel A) were able to tolerate concentrations of syringate up to at least 120 mM, the highest concentration tested, though increasing concentrations resulted in an increasing lag in growth and slower growth rate. In the case of SAL, both CJ486 (see FIG. 10 Panel A) and KT2440 (see FIG. 10 Panel B) were able to grow in the presence of 20 mM after a considerable lag, but neither strain was able to grow at a concentration of 50 mM of substrate. As expected, CJ486 grew to higher ODs when provided with SA or SAL as a result of its ability to metabolize these substrates relative to KT2440 which grew only on the glucose provided. Gallate (see FIG. 11) was slightly more toxic than SAL, resulting in greater lags in growth and slower growth rates. Again, 20 mM was the highest concentration that allowed growth, which was completely inhibited at a concentration of 50 mM. More growth was not observed with the addition of gallate relative to KT2440.

Figure 12:
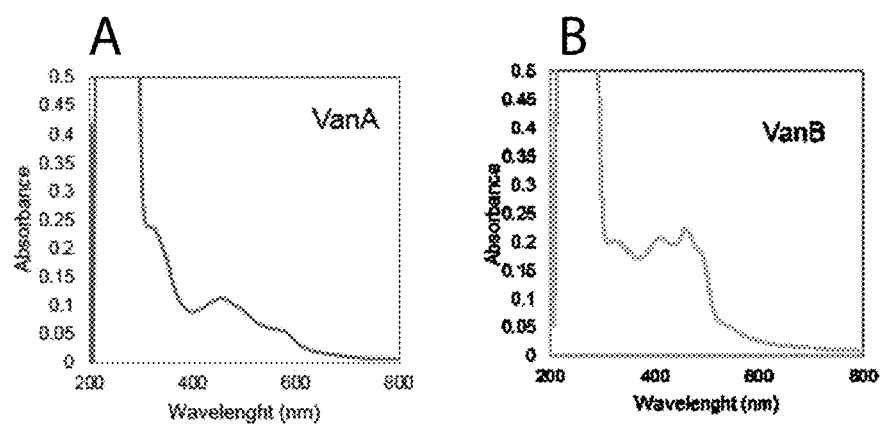
FIG. 12 illustrates UV/vis spectra of purified VanA (Panel A) and VanB (Panel B), according to some embodiments of the present disclosure.
Figure 20:
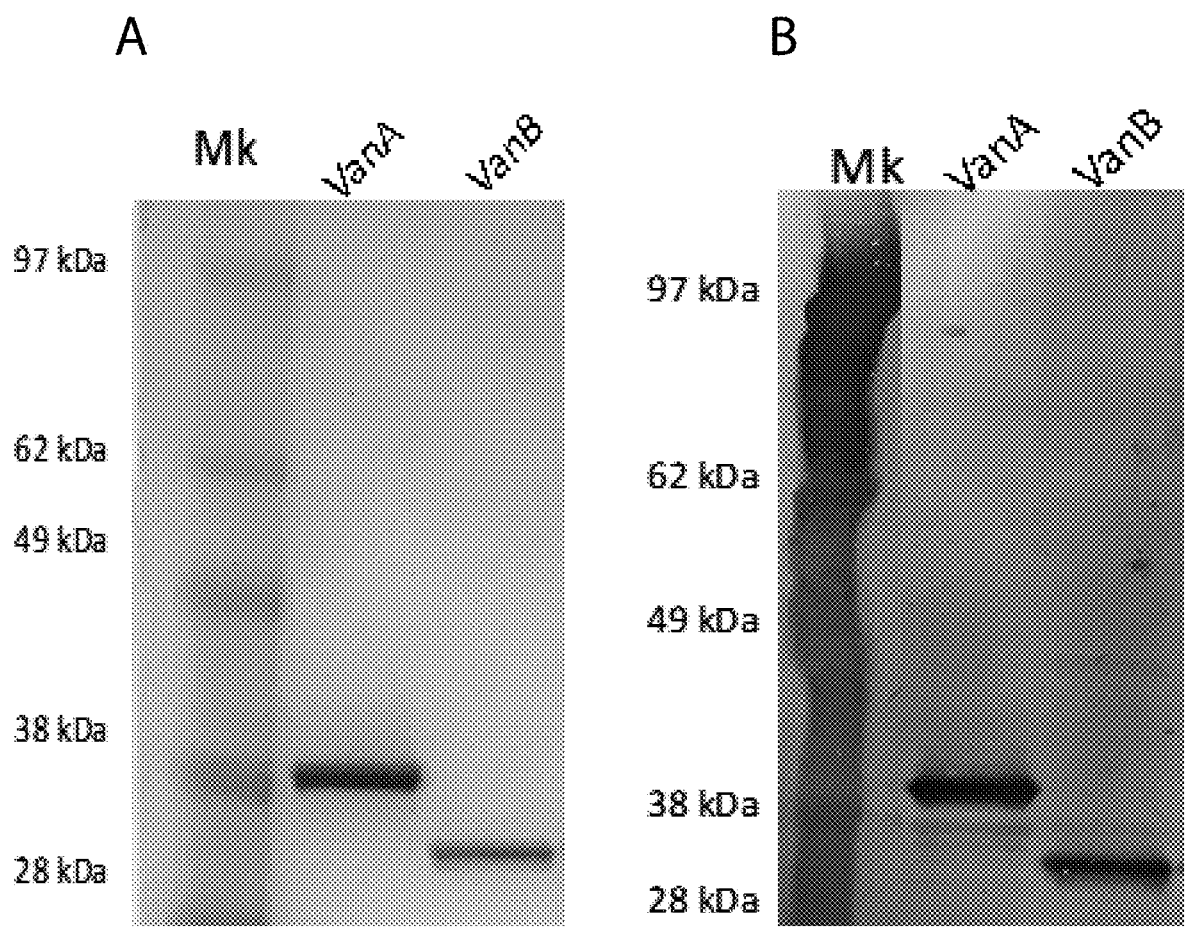
FIG. 20 illustrates SDS-PAGE (Comassie staining) results of purified VanA and VanB (Panel A); and Western-Blot analysis of purified VanA and VanB (Panel B), both according to some embodiments of the present disclosure.
Figure 21:
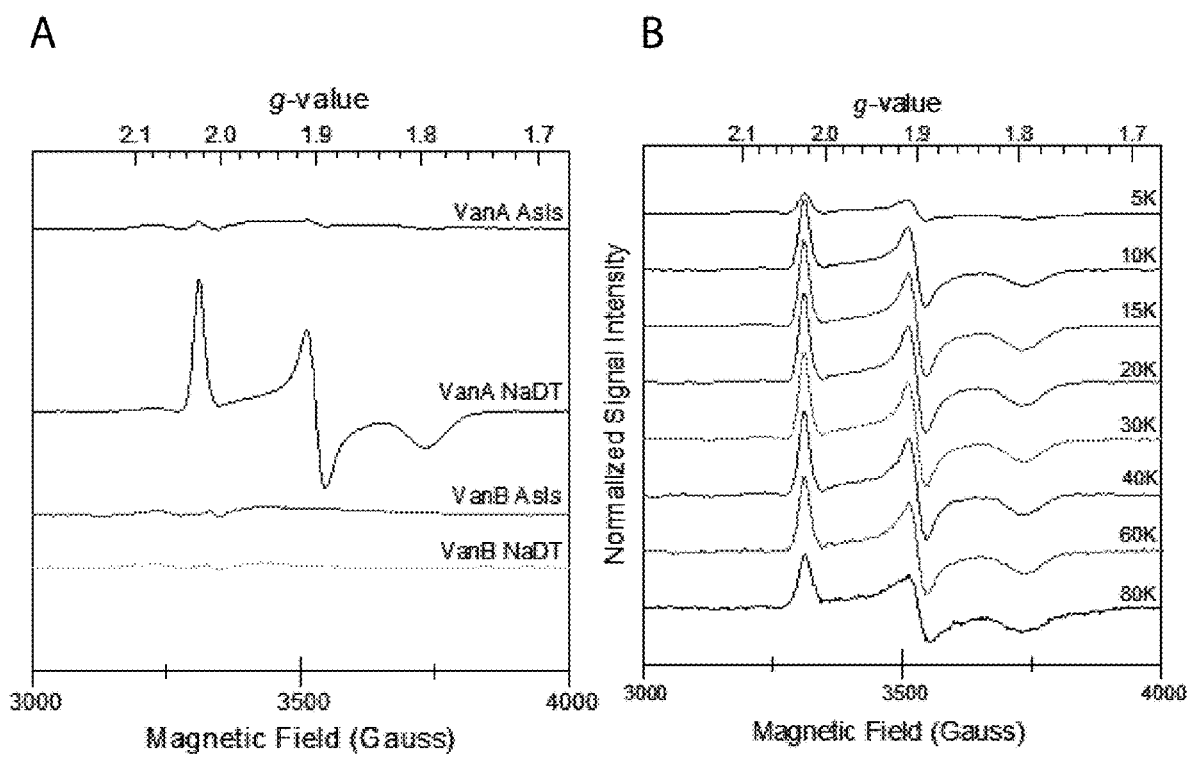
FIG. 21 illustrates EPR results of as is (as isolate) and NaDT (reduced) purified VanA and VanB (Panel A). The rhombic signal upon reduction of VanA (blue line) is indicative of an S=½ [2Fe-2S]1+ cluster; Temperature profile of the rhombic signal for NaDT reduced VanA (Panel B). The signal could be observed up to 80 K and was most intense in the 20 to 30 K range, consistent with [2Fe-2S] cluster temperature properties. Signal intensities were normalized for the Curie law.
Figure 22:
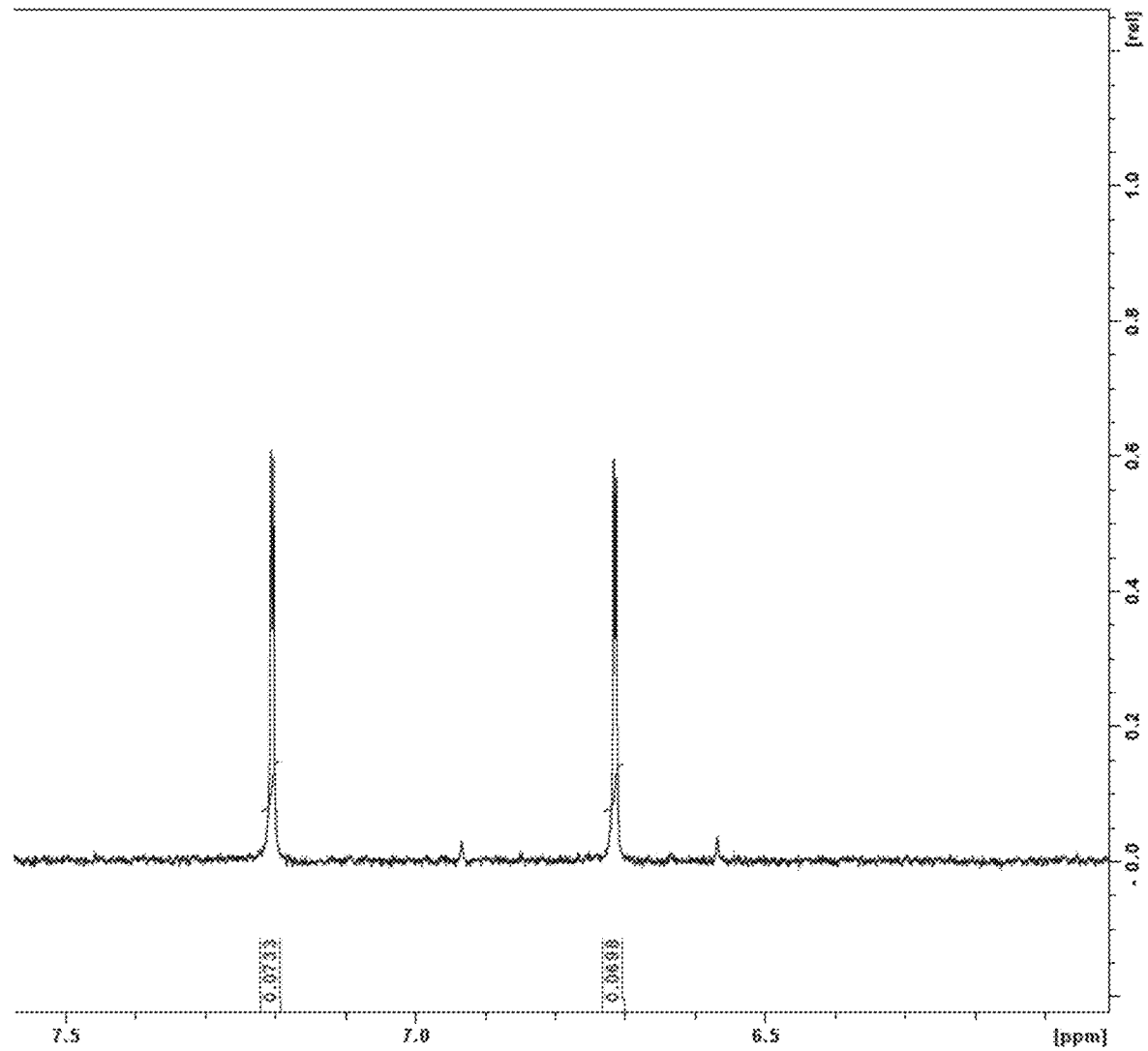
FIG. 22 illustrates NMR spectra of PDC produced by SN266 after 96 h fermentation in shake flasks, according to some embodiments of the present disclosure.
Figure 23:
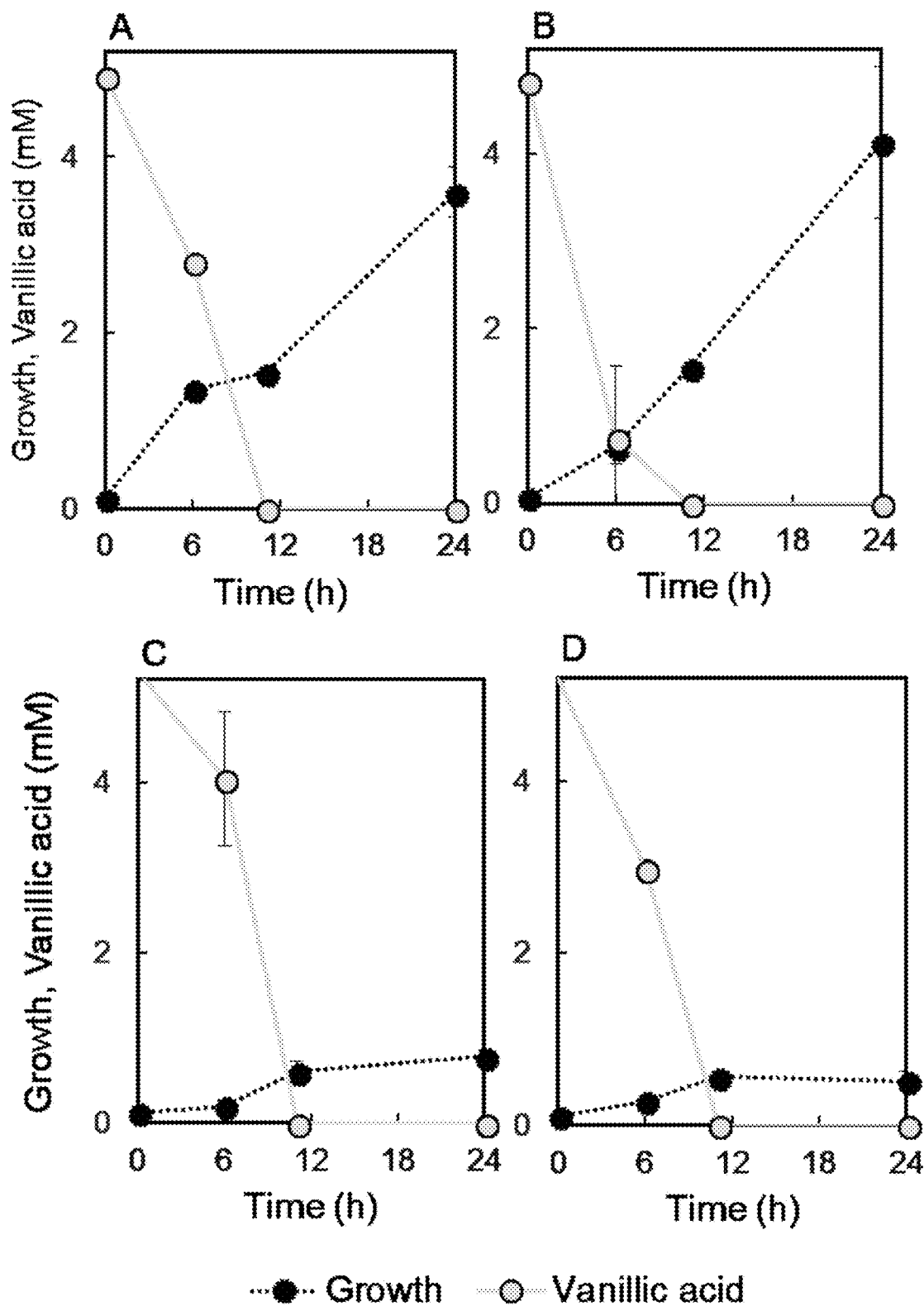
FIG. 23 illustrates *P. putida* KT2440 wild-type and CJ486 (second copy vanAB overexpressed in genome) grown in M9 minimal medium containing 5 mM vanillate, in the presence (Panels A&B) and in absence of glucose (Panels C&D), both according to some embodiments of the present disclosure. Culture was sampled periodically to evaluate growth by $OD_{600}$ and metabolite concentrations in the media using HPLC.

VanAB Enzyme Production and Spectra:

These results indicate that VanAB is an important enzyme in the S-lignin degradation pathway of *P. putida* KT2440. To examine these proteins in vitro, the two subunits VanA and VanB were expressed recombinantly separately in *E. coli* and purified by His-Tag chromatography (SDS protein gel and Western Blot, see FIG. 20 Panels A and B). VanA UV/vis spectra (see FIG. 12 Panel A) shows a shoulder at 480 nm, most likely due to the presence of the 2Fe-2S cluster and VanB spectra (see FIG. 12 Panel B) is characterized by a peak at 420 nm, which is typical for FAD/FNM associated protein. The electron paramagnetic resonance (EPR) analysis is in accordance with the UV/vis spectra obtained, demonstrating VanA subunit as the only redox active [2Fe-2S] cluster protein.

Figure 13:
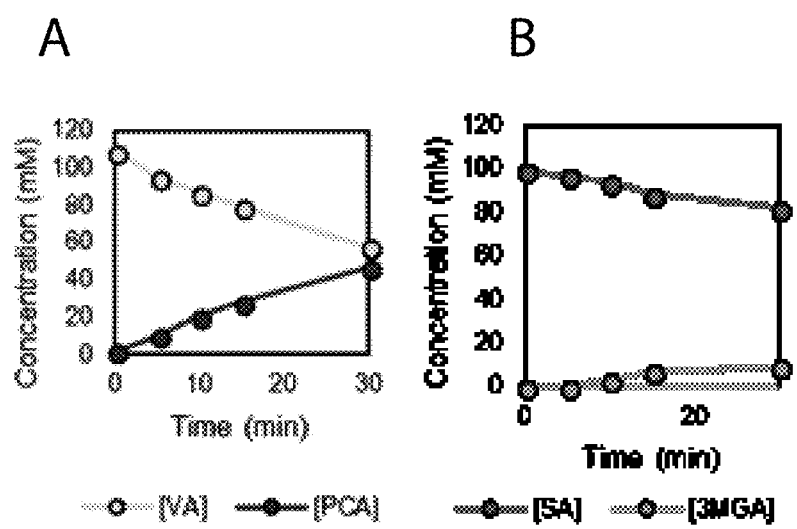
FIG. 13 illustrates time course of VA consumption/PCA production and SA consumption/3-MGA production, according to some embodiments of the present disclosure. VanAB (1.3 µM) was incubated with 100 µM VA or SA at room temperature, in the presence of 0.5 µM NADPH. Results are an average of at least two experiments.
Figure 14:
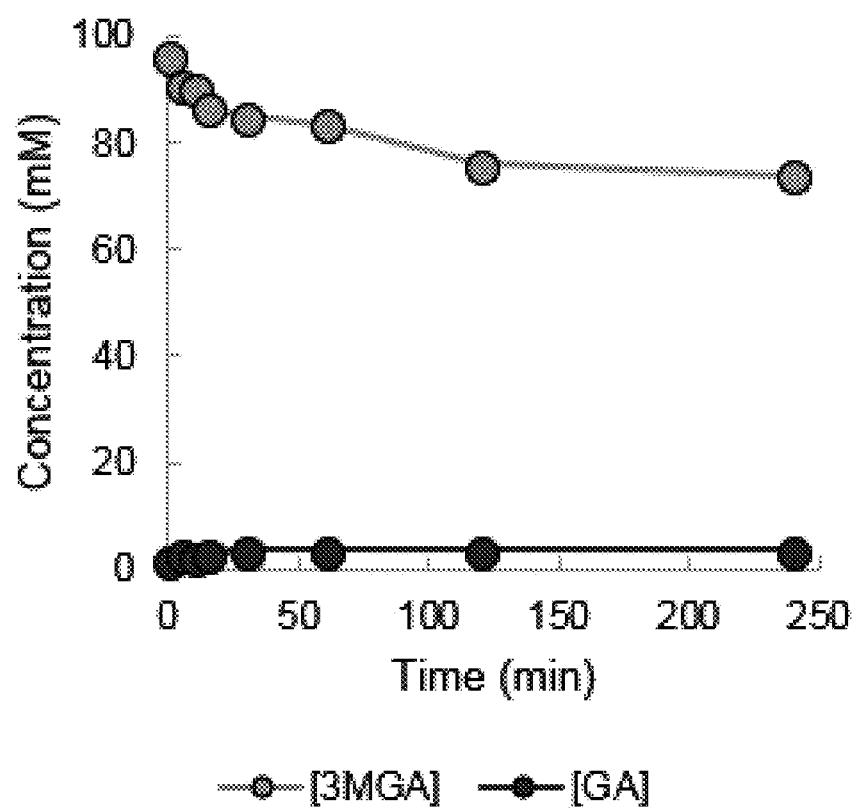
FIG. 14 illustrates time-course of 3MGA consumption and GA formation, according to some embodiments of the present disclosure.

In Vitro Analyses of Vanillate and Syringate Consumption:

To corroborate the in vivo results, activity assays were performed using the purified VanA and VanB subunits towards VA and SA substrates (see FIG. 13 and FIG. 14). 30 minutes time course reaction demonstrated the conversion of 58 µM of VA metabolized into protocatechuate product (almost 1:1 molar ratio, with 47 µM product formed). The consumption of SA (and 3-MGA) was slower, with a residual SA concentration of 70 µM and 9 µM of 3-MGA produced.

Figure 15:
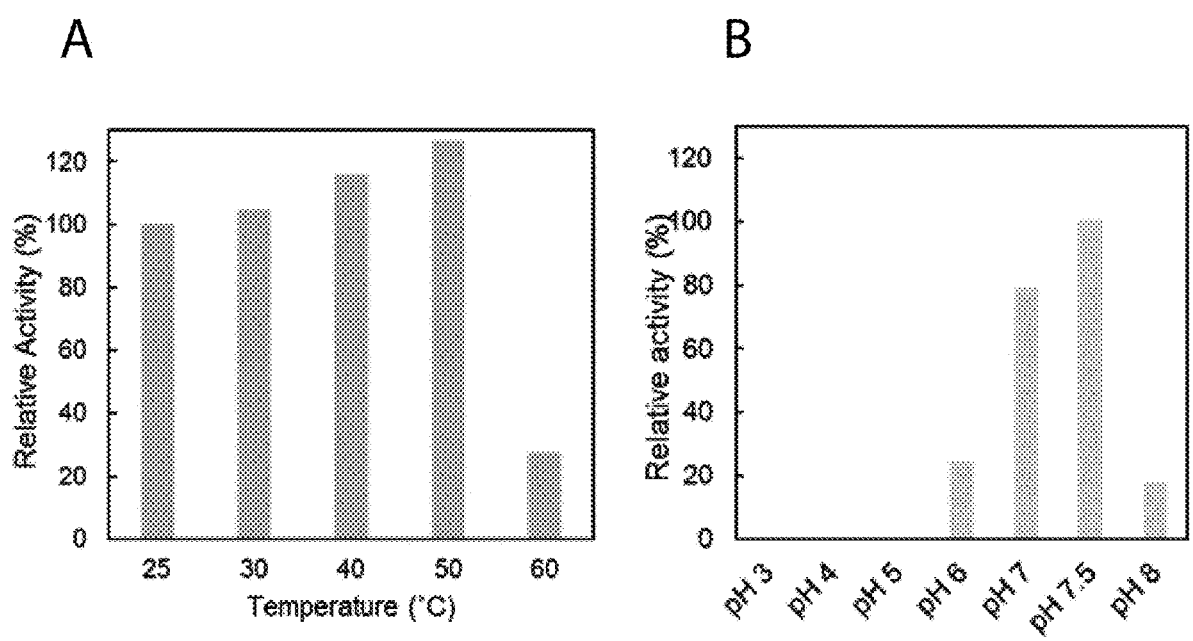
FIG. 15 illustrates VanAB optimum temperature results, all according to some embodiments of the present disclosure; (Panel A); VanAB Optimal pH (Panel B).
Figure 16:
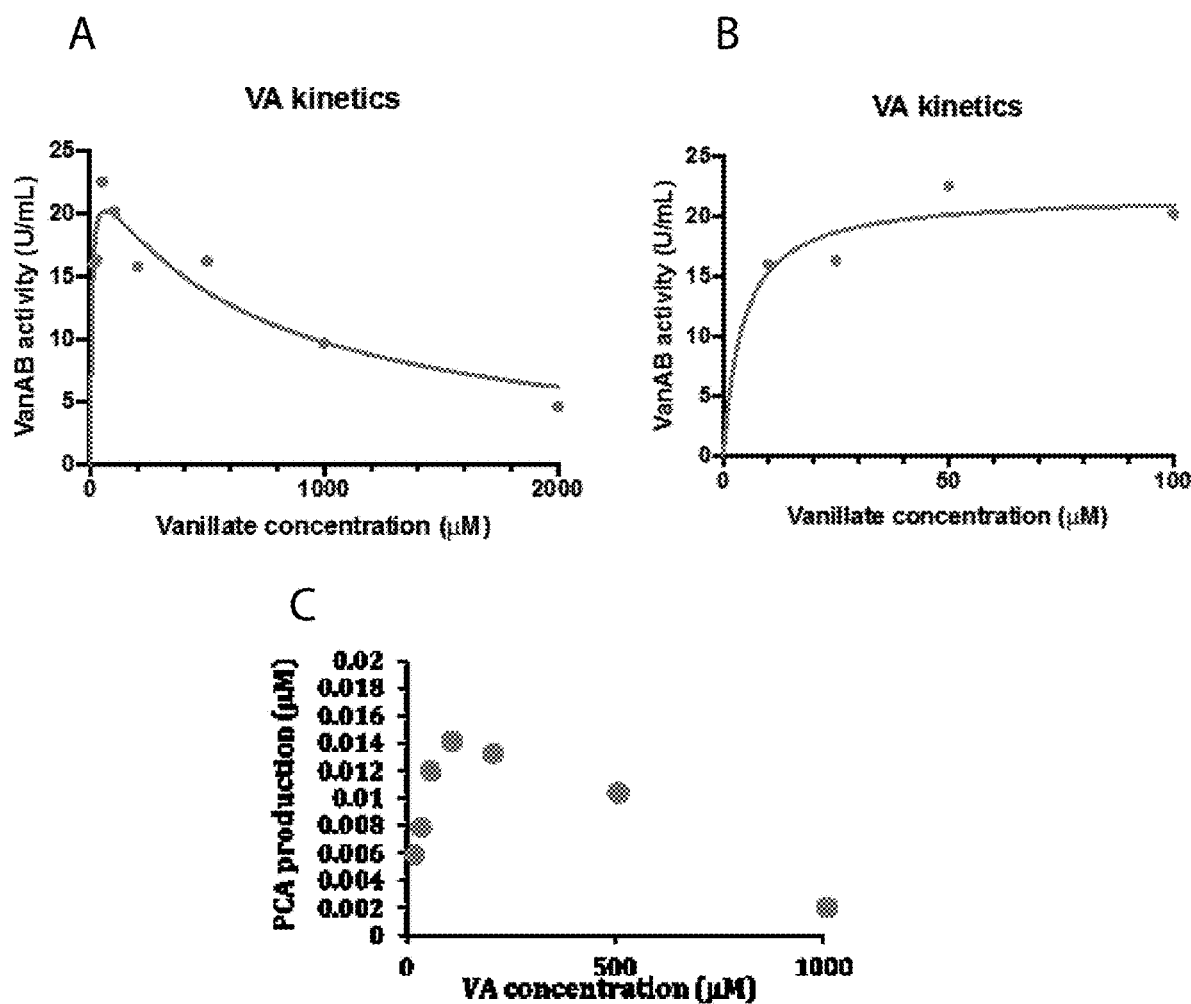
FIG. 16 illustrates VA substrate inhibition kinetics, according to some embodiments of the present disclosure: (Panel A and Panel B) VA apparent kinetics, and (Panel C) VA substrate inhibition kinetics analyzed as PCA production by means of HPLC.
Figure 17:
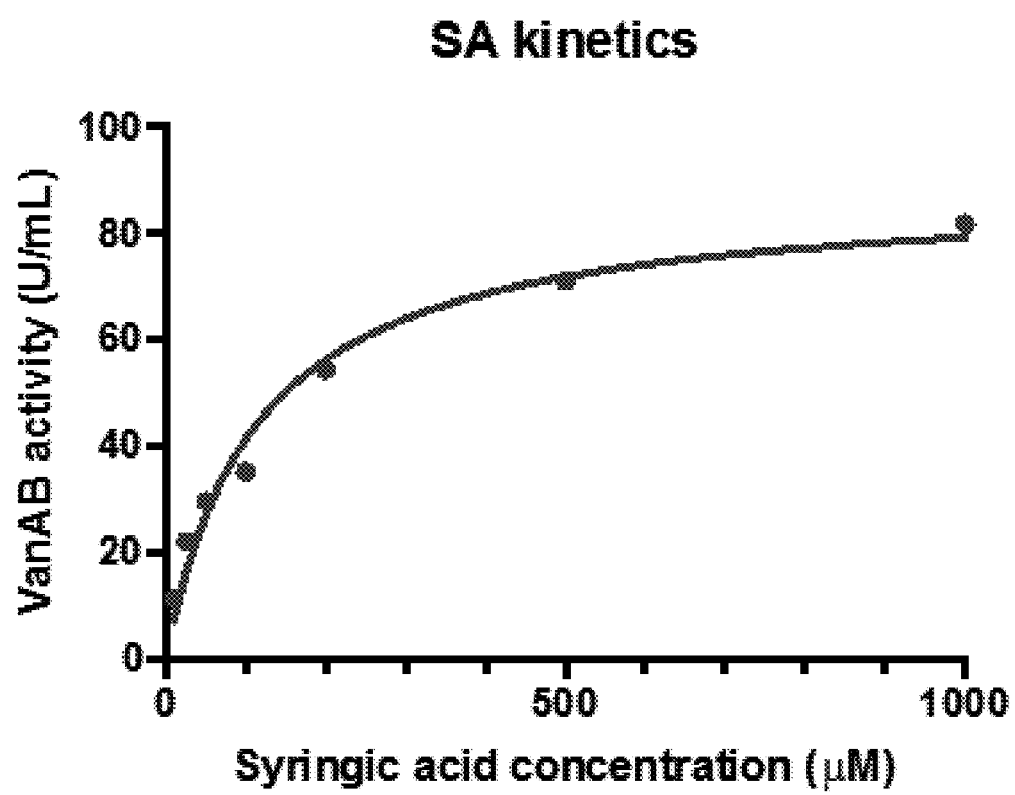
FIG. 17 illustrates SA Michalis-Menten kinetics, according to some embodiments of the present disclosure.
Figure 18:
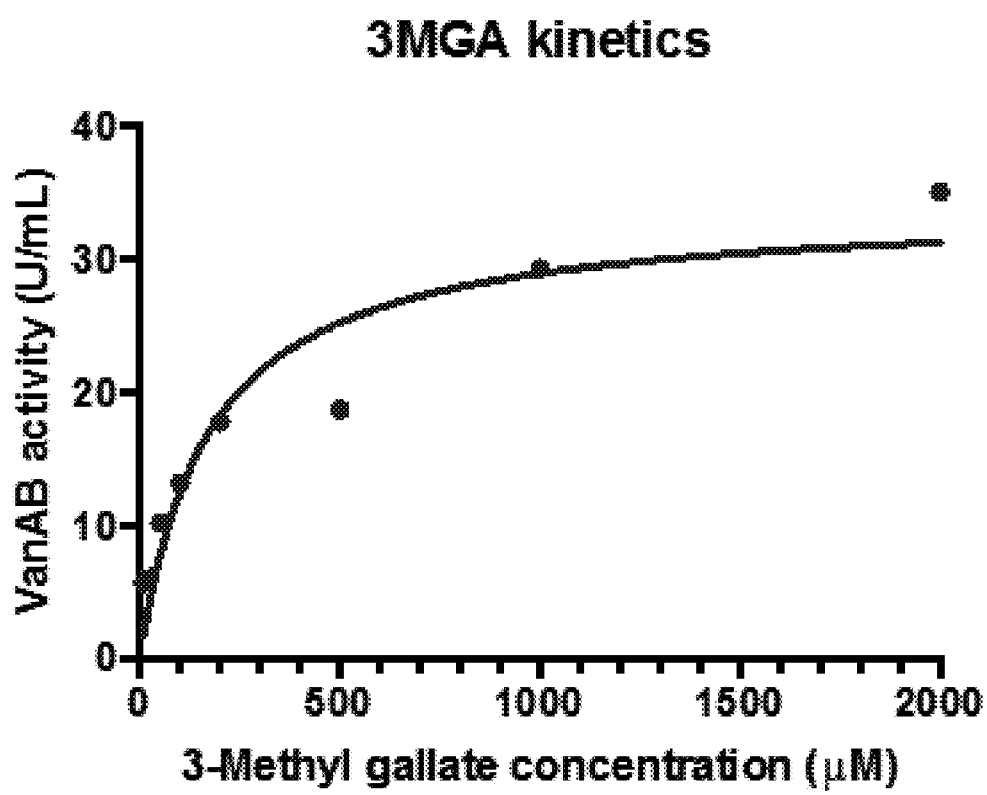
FIG. 18 illustrates 3-MGA Michalis-Menten kinetics, according to some embodiments of the present disclosure.
Figure 19:
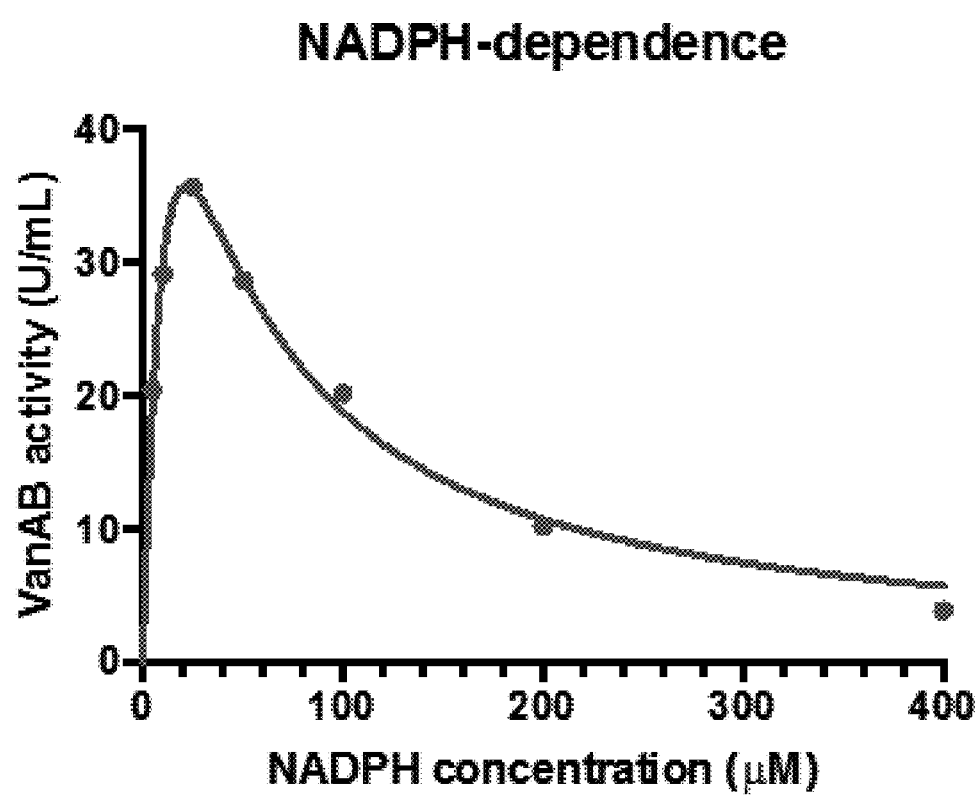
FIG. 19 illustrates NADPH-dependence, according to some embodiments of the present disclosure.

Kinetics Characterization of VanA and VanB System:

Further characterizations showed an optimal temperature of 30° C. and an optimum pH of 7.5 for VanAB (see FIG. 15 Panels A and B). Moreover, it was revealed that this enzyme followed a substrate inhibition kinetics in the presence of VA (see FIG. 16 Panels A-C), with a $k_i$ of 426.2±271.1 µM, whilst a Michaelis-Menten kinetics was followed in the case of both SA (see FIG. 17) and 3MGA (see FIG. 18), with a $k_{cat}$ of 67.8±4.1 min$^{-1}$ and 26.1±2.8 min$^{-1}$, respectively. Interestingly, a NADPH dependent inhibition was shown for VanAB in the presence of VA, with a $k_i$ of 25.3±7.4 µM (see FIG. 19). The kinetics constants evaluated for VA, SA, 3-MGA and NADPH are summarized in Table 4 below. VanAB activity was also tested towards vanillate analogous substrates such as vanillin, ferulic acid, sinapinic acid, methyl vanillate, ethyl vanillate, and guaiacol. VanAB showed catalytic activity towards guaiacol (188±16 U/mg), ethyl vanillate (100±27 U/mg), and towards vanillin, for which a 10-fold lower specific activity was measured in comparison to VA (49±18 U/mg) (see Table 5 below).

TABLE 4 kinetics constants measured for VanAB in the presence of VA, SA, 3-MGA, and in dependence of NADPH concentration.

| Substrate | $K_M$ (µM) | $K_{Mapp}$ (µM) | $K_{cat}$ (min$^{-1}$) | $K_{cat}^{app}$ (min$^{-1}$) | $K_i$ (µM) |
|---|---|---|---|---|---|
| Vanillate | n/a | 4.3 ± 3.1 | n/a | 16.8 ± 1.9 | 426.2 ± 26.21 |
| Syringate | 113.9 ± 21.5 | n/a | 67.8 ± 4.1 | n/a | n/a |
| 3-MGA | 172.4 ± 64.6 | n/a | 26.1 ± 2.8 | n/a | n/a |
| NADPH | n/a | 26.7 ± 3.7 | n/a | 2.7 ± 1.1 | 25.3 ± 7.4 |

TABLE 5

VanAB activity tested towards analogous substrates

| Substrate | VanAB specific activity (U/mg) |
|---|---|
| Vanillate | 403 ± 59 |

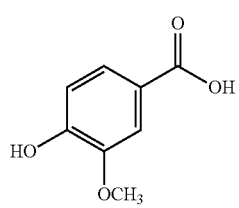 [SMILES: COc1cc(C(=O)O)ccc1O]

| | |
|---|---|
| Syringate | 704 ± 103 |

| | |
|---|---|
| 3-MGA | 264 ± 86 |

| | |
|---|---|
| Vanillin | 49 ± 18 |

| | |
|---|---|
| Methyl vanillate | n.d. |

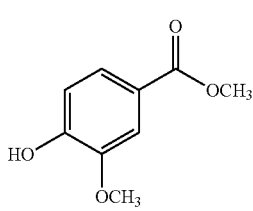 [SMILES: COC(=O)c1ccc(O)c(OC)c1]

TABLE 5-continued

VanAB activity tested towards analogous substrates

| Substrate | VanAB specific activity (U/mg) |
|---|---|
| Sinapinic acid | n.d. |
| Guieicol | 188 ± 16 |
| Ferulic Acid | n.d. |
| Ethylvanillate | 100 ± 27 |

PDC Production:

Studied next was the conversion of the S-lignin monomer syringate to PDC, a precursor of biopolymer from syringyl-type lignin. The natural capabilities of *P. putida* KT2440 CJ486 based strain to convert 3-MGA and gallate into PDC by overexpressing 4,5-dioxygenase type enzyme, GalA and 3,4-dioxygenase type enzyme, PcaHG were studied. The strains built were SN249, lacking GalA only, SN253, lacking pcaHG gene only and SN255 lacking both enzymes (GalA and pcaHG). Additionally, strains SN265 and SN266 were constructed, overexpressing pcaHG (tac promoter integrated upstream of the gene), CJ486 based strain only and CJ486 based strain lacking GalA, respectively. The performance of the engineered strains was evaluated in shake flasks, with addition of 5 mM syringic acid in the presence of 20 mM glucose. Strain SN255 was unable to produce any PDC, strain SN249 was able to accumulate some PDC via pcaHG activity, however strain SN253 did not produce any PDC products and this was due to the fact that GalA was also able to metabolize gallic acid, further converted before entering TCA cycle. The most efficient strain was SN266 with 3.4 mM PDC (about 68% of substrate converted into PDC) produced after three days. All the results are summarized in Table 6 below.

TABLE 6

PDC production by *P. putida* KT2440 engineered strains after 72 hours

| Strains | Genotype | PDC (mM) | Yield (%) |
|---|---|---|---|
| SN249 | Ptac:vanAB*Δga/A | 0.50 ± 0.06 | 10.1 |
| SN253 | Ptac:vanAB* ΔpcaHG | 0 | 0 |
| SN255 | Ptac:vanAB* ΔpcaHG ΔgalA | 0 | 0 |
| SN265 | Ptac:vanAB* Ptac:pcaHG | 1.56 ± 0.5 | 31.2 |
| SN266 | Ptac:vanAB* Ptac:pcaHG ΔgalA | 3.38 ± 0.43 | 67.7 |

*second copy vanAB integrated into the genome

Materials and Methods

Plasmids construction: DNA fragments and primers were synthesized by Integrated DNA Technologies (IDT) or alternatively amplified from *P. putida* genomic DNA using Q5® Hot Start Fidelity 2x Master Mix (New England Biolabs) by polymerase chain reaction (PCR). Plasmids were constructed using NEBuilder® HiFi DNA Assembly Master Mix and transformed into competent cells NEB 5-alpha F *Escherichia coli* (New England Biolabs). Transformants were selected on LB Lennox medium plates (10 g/L tryptone, 5 g/L yeast extract, 5 g/L NaCl, and 15 g/L agar) supplemented with the appropriate antibiotic (ampicillin 100 µg/m or kanamycin 50 µg/mL) and grown at 37° C. GENEWIZ Inc. performed Sanger sequencing on all our plasmid inserts to confirm the correct sequence (plasmid construction details and the sequence of primers and DNA fragments is provided in the supplementary information).

Strain Construction:

Gene deletion, insertion or replacement in *P. putida* KT2440 was performed by the antibiotic/sacB counter-selection method. The suicide integration vector was transformed into cells of the targeted strain by electroporation. Transformants for recombination of the plasmid into the genome were selected on LB medium supplemented with tetracycline 10 µg/mL or kanamycin 50 µg/mL and the counter selection for recombination of the plasmid out of the genome was done by restreaking single colonies on YT+25% sucrose plates (20 g/L tryptone, 10 g/L yeast extract, 250 g/L sucrose, and 18 g/L agar). *P. putida* was grown at 30° C. The diagnostic colony PCR was performed with MyTaq® HS Red Mix (Bioline) to confirm gene deletion, addition or replacement (see supplementary information for primer sequences).

Cell Cultivation, Protein Expression and Purification:

A seed culture from one colony of *Escherichia. coli* (*E. coli*) transformed with plasmid containing VanAB (Strain X), codon optimized for overexpression in *E. coli*, was used to inoculate 2-L Erlenmeyer shake flask using rich complex media (need recipe) for cell cultivation and protein expression aerobically. Cells were grown at 37° C., 180 rpm until an $OD_{600}$ of 1 was reached before induction with IPTG and protein expression performed at 16° C., 180 rpm. After 16-20 h of protein expression, the cells were harvested and disrupted before protein purification via His-tag technique. Following the purification method, dialysis was performed to exchange the buffer and 1 mM dithiothreitol (DTT) was added for enhancement of protein stability.

In Vitro Assays:

Enzymatic assays were performed using 100 µM substrate vanillate (VA), syringic acid (SA), 3-MGA or analogous substrates for activity assay and different increased concentrations of substrates for kinetics analysis in the presence of 50 µM/mL of VanA and VanB purified enzyme subunits, 100 µM cofactor NADPH in 20 mM Tris-HCL buffer, pH 7.5.

Activity assay were followed by cofactor NADPH consumption monitored spectrophotometrically at 340 nm.

In Vivo Reactions:

Strains were cultivated overnight in LB medium, washed once with 1×M9 medium (6.78 g/L disodium phosphate, 3 g/L monopotassium phosphate, 0.5 g/L NaCl, 1 g/L $NH_4Cl$, 2 mM $MgSO_4$, 100 μM $CaCl_2$), and 18 μM $FeSO_4$, pH 7.0) and used to inoculate 125 mL baffled flasks containing M9 minimal media supplemented with various concentrations of S-lignin monomers (SA, 3-MGA or syringaldehyde (SAL), stock solution dissolved in 2% DMSO) and 20 mM glucose in some cases, to an optical density of 0.1 and incubated shaking at 225 rpm, 30° C. Cultures were sampled periodically by removing 1 mL that was used to measure the $OD_{600}$ using a spectrophotometer (DU640 Beckman Coulter). In the case of 3-MGA provided to wild-type strain KT2440, SN166 and SN175, the reaction was downscaled to 50 mL baffled flasks containing 10 mL minimal media and the experiment was performed in duplicate.

Metabolites analysis: Samples from the in vivo experiments were centrifuged to remove the cells and the supernatants were filtered through a 0.2 μm syringe filter and metabolite concentrations were analyzed on an Agilent 1100 series HPLC equipped with Phenominex Rezex™ RFQ-Fast Acid $H^+$ (8%), LC Column, a diode array detector, and refractive index detector and a 0.01 N $H_2SO_4$ mobile phase. The products were identified by comparing the retention times and spectral profiles with pure compounds. Shake flask experiments were performed in triplicate and the standard deviation of the triplicate measurement were calculated using the following equation: in which x is each value in a sample, x is the average of the values, and n is the number of values. The same method was employed to analyze the metabolites from the in vitro reaction. PDC compounds was analyzed and quantified by $^1$H NMR spectrum. 2004, of fermentation broth was diluted in 400 μL of deuterium oxide (Isotope Laboratories Inc.) and 50 μL of deuterium oxide containing known mass of the internal standard succinic acid.

Proteomics and RNA-Seq:

A seed culture of P. putida KT2440 WT and CJ486 were grown overnight in LB and used to inoculate 1 L preculture of 1×M9 minimal medium supplemented with 20 mM glucose in 2 L flask. The cells were grown until they reached log phase ($OD_{600}$ 0.5-0.7), then washed one time with 1×M9 minimal medium (to remove any trace of glucose), then concentrated and used to inoculate 500 mL flask containing 100 mL of 1×M9 minimal medium supplemented with the different substrates (VA or SA in the presence or absence of glucose and glucose only). Triplicate were used in this experiment and the cells were grown until they reached log phase of $OD_{600}$ 0.3, then they were split evenly into 50 mL falcon tubes, centrifuged at 4° C., 4100 rpm, for 5 min and fixed in liquid nitrogen before being stored at −80° C. until further analysis for proteomics or RNA-seq.

Plasmid construction, bacterial strain construction, and primer details are provided as detailed in Tables 1-3.

A "vector" or "recombinant vector" is a nucleic acid molecule that is used as a tool for manipulating a nucleic acid sequence of choice or for introducing such a nucleic acid sequence into a host cell. A vector may be suitable for use in cloning, sequencing, or otherwise manipulating one or more nucleic acid sequences of choice, such as by expressing or delivering the nucleic acid sequence(s) of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art.

Typically, an expression vector includes at least one nucleic acid molecule of interest operatively linked to one or more expression control sequences (e.g., transcription control sequences or translation control sequences). In one aspect, an expression vector may comprise a nucleic acid encoding a recombinant polypeptide, as described herein, operably linked to at least one regulatory sequence. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the sequences described herein for simple cloning or protein expression.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning or assembling into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

A nucleic acid molecule or polynucleotide can include a naturally occurring nucleic acid molecule that has been isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having enzyme activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme. For example, a fragment can comprise the minimum nucleotides required to encode a functional enzyme. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to a sequence represented herein. In other embodiments, the nucleic acids may be at least about 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein, or 80%, 81%, 82%, 83%, 84%, 85%, 86%, 87%, 88%, 89%, 90%, 91%, 92%, 93%, 94%, 95%, 96%, 97%, 98% or 99% identical to a sequences represented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm. As a result of the degeneracy of the genetic code, many nucleic acid sequences can encode a given polypeptide with a particular enzymatic activity. Such functionally equivalent variants are contemplated herein.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, assembling, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes and enzyme cocktails through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as *E. coli*; bacteria from the genera *Pseudomonas* (e.g., *P. putida* or *P. fluorescens*), *Bacillus* (e.g., *B. subtilis, B. megaterium* or *B. brevis*), *Caulobacter* (e.g., *C. crescentus*), *Lactoccocus* (e.g., *L. lactis*), *Streptomyces* (e.g., *S. coelicolor*), *Streptococcus* (e.g., *S. lividans*), and *Corynybacterium* (e.g., *C. glutamicum*); fungi from the genera *Trichoderma* (e.g., *T. reesei, T. viride, T. koningii*, or *T. harzianum*), *Penicillium* (e.g., *P. funiculosum*), *Humicola* (e.g., *H. insolens*), *Chrysosporium* (e.g., *C. lucknowense*), *Gliocladium, Aspergillus* (e.g., *A. niger, A. nidulans, A. awamori*, or *A. aculeatus*), *Fusarium, Neurospora, Hypocrea* (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, *miscanthus*, and trees such as hardwoods and softwoods are also contemplated herein as host cells.

Host cells can be transformed, transfected, or infected as appropriate by any suitable method including electroporation, calcium chloride-, lithium chloride-, lithium acetate/ polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from bacteria or fungi by direct transformation, in which DNA is mixed with the cells and taken up without any additional manipulation, by conjugation, electroporation, or other means known in the art. Expression vectors may be expressed by bacteria or fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing bacteria or fungi, for example, are available from ATCC. Exemplary culture/fermentation conditions and reagents are known. Media may be supplemented with aromatic substrates like guaiacol, guaethol or anisole for dealkylation reactions.

The nucleic acid molecules described herein encode the enzymes with amino acid sequences such as those represented by the SEQ ID NOs presented herein. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented herein, or may include up to a certain integer number of amino acid alterations. Such protein or polypeptide variants retain functionality as enzymes, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences presented herein and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

While the present disclosure relates to engineered strains that utilize enzymes from *P. putida* KT2440, similar strains could be constructed in different hosts using different endogenous or exogenous enzymes that catalyze the same reactions described herein. Thus, variations to these pathways present in other organisms that may enable the production of the compounds targeted here, or related molecules not described herein, are considered within the scope of the present disclosure.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A genetically modified *Pseudomonas* comprising: a genetic modification resulting in the overexpression of a vanillate demethylase, wherein: the *Pseudomonas* metabolizes S-lignin decomposition molecules consisting of syringate and 3-O-methyl gallate, and the genetically modified *Pseudomonas* produces gallate.

2. The genetically modified *Pseudomonas* of claim 1, wherein the vanillate demethylase is VanAB.

3. The genetically modified *Pseudomonas* of claim 1, wherein the genetically modified *Pseudomonas* produces at least one of 2-hydroxy-2H-pyran-4,6-dicarboxylic acid (PDC), (1E,3E)-4-hydroxybuta-1,3-diene-1,2,4-tricarboxylic acid, (1E)-4-oxobut-1-ene-1,2,4-tricarboxylic acid, 2-hydroxy-4-oxobutane-1,2,4-tricarboxylic acid, oxaloacetate, or pyruvate.

4. The genetically modified *Pseudomonas* of claim 1, further comprising a genetic modification resulting in the expression of a 3,4-dioxygenase.

5. The genetically modified *Pseudomonas* of claim 4, wherein the 3,4-dioxygenase is protocatechuate 3,4-dioxygenase (PcaHG).

6. The genetically modified *Pseudomonas* of claim 5, further comprising an endogenous genetic deletion that causes a lack of expression of a dioxygenase.

7. The genetically modified *Pseudomonas* of claim 6, wherein: the dioxygenase comprises GalA, and the genetically modified *Pseudomonas* produces PDC.

8. The genetically modified *Pseudomonas* of claim 1, wherein the *Pseudomonas* is *P. putida* KT2440.

9. A method for making at least one of 2-hydroxy-2H-pyran-4,6-dicarboxylic acid (PDC), (1E,3E)-4-hydroxybuta-1,3-diene-1,2,4-tricarboxylic acid, (1E)-4-oxobut-1-ene-1,2,4-tricarboxylic acid, 2-hydroxy-4-oxobutane-1,2,4-tricarboxylic acid, oxaloacetate, or pyruvate comprising exposing a genetically modified *Pseudomonas* to a solution containing at least one of S-lignin decomposition molecules, syringate or 3-O-methyl gallate wherein the genetically modified *Pseudomonas* cell comprises a genetic modification that results in the overexpression of vanillate demethylase.

10. The method of claim 9 wherein the vanillate demethylase is VanAB.

11. The method of claim 9 wherein the genetically modified *Pseudomonas* further comprises a genetic modification resulting in the expression of a 3,4-dioxygenase.

12. The method of claim 11, wherein the 3,4-dioxygenase comprises is protocatechuate 3,4-dioxygenase (PcaHG).

13. The method of claim 9 wherein the genetically modified *Pseudomonas* further comprises an endogenous genetic deletion that causes a lack of expression of a dioxygenase.

14. The method of claim 13 wherein the dioxygenase comprises GalA, and the genetically modified *Pseudomonas* produces PDC.

15. The method of claim 14 wherein the modified *Pseudomonas* produces PDC at a concentration of up to 3.38 mM.

16. The method of claim 15 wherein the modified *Pseudomonas* produces up to 3.38 mM PDC after about 72 hours of growth at a yield of up to 68%.

* * * * *

SEQUENCE LISTING

```
<160> NUMBER OF SEQ ID NOS: 28

<210> SEQ ID NO 1
<211> LENGTH: 69
<212> TYPE: DNA
<213> ORGANISM: Artificial Sequence
<220> FEATURE:
<223> OTHER INFORMATION: primer CJ369

<400> SEQUENCE: 1
gtgagcggat aacaatttca cactctagag aggaggacag ctatgtaccc caaaaacacc      60
tggtacgtc                                                              69

<210> SEQ ID NO 2
<211> LENGTH: 52
<212> TYPE: DNA
<213> ORGANISM: Artificial Sequence
<220> FEATURE:
<223> OTHER INFORMATION: primer CJ370

<400> SEQUENCE: 2
tggagtctga ggctcgtcct gaatgatatc tcagatgtcc agcaccagca gc              52

<210> SEQ ID NO 3
<211> LENGTH: 29
<212> TYPE: DNA
<213> ORGANISM: Artificial Sequence
```

```
<220> FEATURE:
<223> OTHER INFORMATION: primer CJ160

<400> SEQUENCE: 3
gatatcattc aggacgagcc tcagactcc                                29

<210> SEQ ID NO 4
<211> LENGTH: 36
<212> TYPE: DNA
<213> ORGANISM: Artificial Sequence
<220> FEATURE:
<223> OTHER INFORMATION: primer CJ161

<400> SEQUENCE: 4
ctctagagtg tgaaattgtt atccgctcac aattcc                        36

<210> SEQ ID NO 5
<211> LENGTH: 33
<212> TYPE: DNA
<213> ORGANISM: Artificial Sequence
<220> FEATURE:
<223> OTHER INFORMATION: primer CJ548

<400> SEQUENCE: 5
gtgtggaatt gtgagcggat aacaatttca cac                           33

<210> SEQ ID NO 6
<211> LENGTH: 60
<212> TYPE: DNA
<213> ORGANISM: Artificial Sequence
<220> FEATURE:
<223> OTHER INFORMATION: primer CJ549

<400> SEQUENCE: 6
gcctccggtc ggaggctttt gactactagt ctgaatgata tctcagatgt ccagcaccag    60

<210> SEQ ID NO 7
<211> LENGTH: 62
<212> TYPE: DNA
<213> ORGANISM: Artificial Sequence
<220> FEATURE:
<223> OTHER INFORMATION: primer CJ301

<400> SEQUENCE: 7
agtgagcgca acgcaattaa tgtgagttag aagccgaatg tcgatgatat ctacaacctg    60
ag                                                                  62

<210> SEQ ID NO 8
<211> LENGTH: 46
<212> TYPE: DNA
<213> ORGANISM: Artificial Sequence
<220> FEATURE:
<223> OTHER INFORMATION: primer CJ302

<400> SEQUENCE: 8
gattaattgt caacagctcg aattcaaaaa accgcacctg ggtgcg              46

<210> SEQ ID NO 9
<211> LENGTH: 68
<212> TYPE: DNA
<213> ORGANISM: Artificial Sequence
<220> FEATURE:
<223> OTHER INFORMATION: primer CJ306

<400> SEQUENCE: 9
```

-continued gtaaactagt agtcaaaagc ctccgaccgg aggcttttga ctcatggatg cctgaaaggc    60
tcccttac    68

<210> SEQ ID NO 10
<211> LENGTH: 54
<212> TYPE: DNA
<213> ORGANISM: Artificial Sequence
<220> FEATURE:
<223> OTHER INFORMATION: primer CJ307

<400> SEQUENCE: 10
ccctgagtgc ttgcggcagc gtgaagctag gcccctctgg agaatcgaac gatg    54

<210> SEQ ID NO 11
<211> LENGTH: 19
<212> TYPE: DNA
<213> ORGANISM: Artificial Sequence
<220> FEATURE:
<223> OTHER INFORMATION: primer CJ290

<400> SEQUENCE: 11
aatacgcaaa ccgcctctc    19

<210> SEQ ID NO 12
<211> LENGTH: 18
<212> TYPE: DNA
<213> ORGANISM: Artificial Sequence
<220> FEATURE:
<223> OTHER INFORMATION: primer CJ291

<400> SEQUENCE: 12
gtagctgaca ttcatccg    18

<210> SEQ ID NO 13
<211> LENGTH: 18
<212> TYPE: DNA
<213> ORGANISM: Artificial Sequence
<220> FEATURE:
<223> OTHER INFORMATION: primer SN103

<400> SEQUENCE: 13
ccactgcgcc agcgacgc    18

<210> SEQ ID NO 14
<211> LENGTH: 18
<212> TYPE: DNA
<213> ORGANISM: Artificial Sequence
<220> FEATURE:
<223> OTHER INFORMATION: primer SN226

<400> SEQUENCE: 14
gcttcaggcg agttggcg    18

<210> SEQ ID NO 15
<211> LENGTH: 18
<212> TYPE: DNA
<213> ORGANISM: Artificial Sequence
<220> FEATURE:
<223> OTHER INFORMATION: primer CJ311

<400> SEQUENCE: 15
agcctcttca gcgtcaac    18

<210> SEQ ID NO 16
<211> LENGTH: 19

```
<212> TYPE: DNA
<213> ORGANISM: Artificial Sequence
<220> FEATURE:
<223> OTHER INFORMATION: primer CJ312

<400> SEQUENCE: 16
cacgcctgct tcattgaac                                                  19

<210> SEQ ID NO 17
<211> LENGTH: 18
<212> TYPE: DNA
<213> ORGANISM: Artificial Sequence
<220> FEATURE:
<223> OTHER INFORMATION: primer CJ550

<400> SEQUENCE: 17
tgcacctgta tgtatgcg                                                   18

<210> SEQ ID NO 18
<211> LENGTH: 20
<212> TYPE: DNA
<213> ORGANISM: Artificial Sequence
<220> FEATURE:
<223> OTHER INFORMATION: primer SN238

<400> SEQUENCE: 18
tgacctactt catgggcctg                                                 20

<210> SEQ ID NO 19
<211> LENGTH: 20
<212> TYPE: DNA
<213> ORGANISM: Artificial Sequence
<220> FEATURE:
<223> OTHER INFORMATION: primer SN239

<400> SEQUENCE: 19
gaagttgaaa cggtccgagg                                                 20

<210> SEQ ID NO 20
<211> LENGTH: 21
<212> TYPE: DNA
<213> ORGANISM: Artificial Sequence
<220> FEATURE:
<223> OTHER INFORMATION: primer CJ054

<400> SEQUENCE: 20
atcggctcgt ataatgtgtg g                                               21

<210> SEQ ID NO 21
<211> LENGTH: 18
<212> TYPE: DNA
<213> ORGANISM: Artificial Sequence
<220> FEATURE:
<223> OTHER INFORMATION: primer CJ163

<400> SEQUENCE: 21
ttgtccagca gggttgtc                                                   18

<210> SEQ ID NO 22
<211> LENGTH: 18
<212> TYPE: DNA
<213> ORGANISM: Artificial Sequence
<220> FEATURE:
<223> OTHER INFORMATION: primer CJ534

<400> SEQUENCE: 22
```
cctcggtgag tttctcc                                                      18

<210> SEQ ID NO 23
<211> LENGTH: 38
<212> TYPE: DNA
<213> ORGANISM: Artificial Sequence
<220> FEATURE:
<223> OTHER INFORMATION: primer CJ100

<400> SEQUENCE: 23
ccgaaaagtg ccacctgacg tcggccttgc tgctgcag                               38

<210> SEQ ID NO 24
<211> LENGTH: 37
<212> TYPE: DNA
<213> ORGANISM: Artificial Sequence
<220> FEATURE:
<223> OTHER INFORMATION: primer CJ101

<400> SEQUENCE: 24
gccgcagctc gagatctgga attgtgagaa cgcctgg                                37

<210> SEQ ID NO 25
<211> LENGTH: 36
<212> TYPE: DNA
<213> ORGANISM: Artificial Sequence
<220> FEATURE:
<223> OTHER INFORMATION: primer CJ102

<400> SEQUENCE: 25
agatctcgag ctgcggccgc ggtgaagctt ggggcc                                 36

<210> SEQ ID NO 26
<211> LENGTH: 40
<212> TYPE: DNA
<213> ORGANISM: Artificial Sequence
<220> FEATURE:
<223> OTHER INFORMATION: primer CJ103

<400> SEQUENCE: 26
gctggatcct ctagtgagct cacgatttcc ccattgccag                             40

<210> SEQ ID NO 27
<211> LENGTH: 19
<212> TYPE: DNA
<213> ORGANISM: Artificial Sequence
<220> FEATURE:
<223> OTHER INFORMATION: primer CJ105

<400> SEQUENCE: 27
caccgaaatc agcaagacg                                                    19

<210> SEQ ID NO 28
<211> LENGTH: 18
<212> TYPE: DNA
<213> ORGANISM: Artificial Sequence
<220> FEATURE:
<223> OTHER INFORMATION: primer CJ106

<400> SEQUENCE: 28
atcttgaacc aacgcacc                                                     18